(12) United States Patent
Shiba et al.

(10) Patent No.: US 10,564,082 B2
(45) Date of Patent: *Feb. 18, 2020

(54) SENSOR HAVING POROUS MATERIAL OR PARTICULATE MATERIAL AS RECEPTOR LAYER

(71) Applicant: NATIONAL INSTITUTE FOR MATERIALS SCIENCE, Ibaraki (JP)

(72) Inventors: Kota Shiba, Ibaraki (JP); Genki Yoshikawa, Ibaraki (JP); Yusuke Yamauchi, Ibaraki (JP); Norihiro Suzuki, Ibaraki (JP); Gaku Imamura, Ibaraki (JP); Kosuke Minami, Ibaraki (JP); Hamish Hei-Man Yeung, Ibaraki (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 156 days.

This patent is subject to a terminal disclaimer.

(21) Appl. No.: 15/543,298

(22) PCT Filed: Aug. 31, 2015

(86) PCT No.: PCT/JP2015/074659
§ 371 (c)(1),
(2) Date: Jul. 13, 2017

(87) PCT Pub. No.: WO2016/121155
PCT Pub. Date: Aug. 4, 2016

(65) Prior Publication Data
US 2018/0003604 A1    Jan. 4, 2018

(30) Foreign Application Priority Data

Jan. 27, 2015 (JP) .................................. 2015-013271
May 15, 2015 (JP) .................................. 2015-100405

(51) Int. Cl.
*G01N 5/00* (2006.01)
*G01N 5/02* (2006.01)
(Continued)

(52) U.S. Cl.
CPC ................. *G01N 5/02* (2013.01); *G01G 3/13* (2013.01); *G01N 21/49* (2013.01); *G01N 27/227* (2013.01);
(Continued)

(58) Field of Classification Search
CPC ........ G01N 27/12; G01N 27/227; G01N 5/02; G01N 29/022; G01N 29/036; G01G 3/13; B82Y 15/00; G01L 1/18
See application file for complete search history.

(56) References Cited

U.S. PATENT DOCUMENTS 6,972,423 B2    12/2005  Welland et al.
8,065,904 B1 *  11/2011  Allendorf ............ G01N 29/022
                                                          73/23.2
(Continued)

FOREIGN PATENT DOCUMENTS

CN    103991836    8/2014
EP    2 767 504    8/2014
(Continued)

OTHER PUBLICATIONS

First Office Action dated May 21, 2019 in corresponding Chinese Application No. 201580073960.3, with English translation.
(Continued)

*Primary Examiner* — Blake A Tankersley
(74) *Attorney, Agent, or Firm* — Wenderoth, Lind & Ponack L.L.P.

(57) ABSTRACT

According to improvement of the receptor layer of various sensors of the type for detecting physical parameters (for example, a surface stress sensor, QCM, and SPR), all of high
(Continued)

sensitivity, selectivity, and durability are achieved simultaneously. A porous material or a particulate material, e.g., nanoparticles, is used in place of a uniform membrane which has been conventionally used as a receptor layer. Accordingly, the sensitivity can be controlled by changing the membrane thickness of the receptor layer, the selectivity can be controlled by changing a surface modifying group to be fixed on the porous material or particulate material, and the durability can be controlled by changing the composition and surface properties of the porous material or particulate material.

19 Claims, 28 Drawing Sheets

(51) Int. Cl.
    *G01G 3/13* (2006.01)
    *G01N 29/02* (2006.01)
    *G01N 29/036* (2006.01)
    *G01N 21/49* (2006.01)
    *G01N 27/22* (2006.01)
    *B82Y 15/00* (2011.01)

(52) U.S. Cl.
    CPC ......... *G01N 29/022* (2013.01); *G01N 29/036* (2013.01); *B82Y 15/00* (2013.01); *G01N 2021/495* (2013.01); *G01N 2291/014* (2013.01); *G01N 2291/021* (2013.01); *G01N 2291/022* (2013.01); *G01N 2291/0256* (2013.01); *G01N 2291/02433* (2013.01)

(56) References Cited

U.S. PATENT DOCUMENTS

| | | |
|---|---|---|
| 2005/0205256 A1 | 9/2005 | DiFoggio |
| 2008/0044925 A1 | 2/2008 | Isojima et al. |
| 2013/0133433 A1 | 5/2013 | Yoshikawa |
| 2014/0364325 A1 | 12/2014 | Calbe et al. |
| 2015/0274516 A1 * | 10/2015 | Ollier ................ B81C 1/00206 438/49 |

FOREIGN PATENT DOCUMENTS

| | | | |
|---|---|---|---|
| JP | 57-24542 | 2/1982 | |
| JP | 10-62320 | 3/1988 | |
| JP | 2003-121329 | 4/2003 | |
| JP | 2004-83501 | 3/2004 | |
| JP | 2009-103518 | 5/2009 | |
| JP | 2010-25728 | 2/2010 | |
| WO | 2005/015198 | 2/2005 | |
| WO | WO-2005119233 A1 * | 12/2005 | ............. B82Y 15/00 |
| WO | 2006/046509 | 5/2006 | |
| WO | 2007/057912 | 5/2007 | |
| WO | 2009/113314 | 9/2009 | |
| WO | 2010/025853 | 3/2010 | |
| WO | WO-2010025853 A1 * | 3/2010 | ........... G01N 29/022 |

OTHER PUBLICATIONS

Office Action dated Jul. 19, 2019 in corresponding European Patent Application No. 15880049.0.
Mark D. Allendorf et al., "Stress-Induced Chemical Detection Using Flexible Metal—Organic Frameworks", Journal of the American Chemical Society, 2008, vol. 130, No. 44, pp. 14404-14405.
Communication pursuant to Article 94(3) EPC dated Feb. 20, 2019 in corresponding European Patent Application No. 15880049.0.
Notification of Reasons for Refusal dated Aug. 6, 2018 in corresponding Japanese patent application No. 2016-571666, with English Machine Translation.
International Search Report dated Nov. 24, 2015 in International Application No. PCT/JP2015/074659.
G. Yoshikawa, "Mechanical Analysis and Optimization of Microcantilever Sensor Coated with a Solid Receptor Film", Appl. Phys. Lett. 98, 173502-1-173502-3 (2011).
G. Yoshikawa, C.J.Y. Lee and K. Shiba, "Effects of Coating Materials on Two Dimensional Stress-Induced Deflection of Nanomechanical Sensors", J. Nanosci. Nanotechnol. 14, 2908-2912 (2013).
W. Heni, L. Vonna and H. Haidara, "Experimental Characterization of the Nanoparticle Size Effect on the Mechanical Stability of Nanoparticle-Based Coatings", Nano Lett. 15, 442-449 (2015).
K. Shiba and M. Ogawa, "Microfluidic synthesis of well-defined sub-micron nanoporous titania spherical particles", Chem. Commun. 6851-6853 (2009).
Yan-Shuo Li, Fang-Yi Liang, Helge Bux, Armin Feldhoff, Wei-Shen Yang, and Juergen Caro, "Molecular Sieve Membrane: Supported Metal.Organic Framework with High Hydrogen Selectivity", Angew. Chem. Int. Ed., 49, 548-551 (2010).
Janosch Cravillon, Simon Muenzer, Sven-Jare Lohmeier, Armin Feldhoff, Klaus Huber, and Michael Wiebcke, "Rapid Room-Temperature Synthesis and Characterization of Nanocrystals of a Prototypical Zeolitic Imidazolate Framework", Chem. Mater. 21, 1410-1412 (2009).
Min Tu, Christian Wiktor, Christoph Roesler and Roland A. Fischer, Rapid room temperature syntheses of zeoliticimidazolate framework (ZIF), Chem. Commun. 2014, 50, 13258-13260.
Lili Jiang and Zhuangjun Fan, "Design of advanced porous graphene materials: from grapheme nanomesh to 3D architectures", Nanoscale, 6, 1922-1945 (2014).
Notification of Reasons for Refusal dated May 16, 2018 in corresponding Japanese patent application No. 2016-571666, with machine translation.
Extended European Search Report dated May 9, 2018 in corresponding European patent application No. 15 88 0049.
Notification of Reasons for Refusal dated Feb. 5, 2019 in corresponding Japanese Patent Application No. 2016-571666 with Machine translation.
Notification of Reasons for Refusal dated Dec. 4, 2018 in corresponding Japanese Application No. 2016-571666 with machine translation.

* cited by examiner

Por-OH = T(3,5-DHP)P = 5,10,15,20-tetrakis(3',5'-dihydroxyphenyl)porphyrin

Zn-Por-OH = Zn-T(3,5-DHP)P =
5,10,15,20-tetrakis(3',5'-dihydroxyphenyl)porphinatozinc(II)

US 10,564,082 B2

SENSOR HAVING POROUS MATERIAL OR PARTICULATE MATERIAL AS RECEPTOR LAYER

TECHNICAL FIELD

The present invention relates to a sensor enabling highly sensitive and selective detection of a sample molecule (i.e., molecule of a material that is the detection subject) by coating the sensor with a porous material or a particulate material.

BACKGROUND ART

In general, the sensor is used for measurement after it is coated with a layer referred to as a "receptor layer" which enables highly sensitive and selective detection of a sample molecule. The material used as a receptor layer includes various types such as molecular self-assembled monolayer, DNA/RNA, protein, antigen/antibody, or polymer. In addition to sensitivity and selectivity, from the viewpoint of reproducibility of measurement or durability of a sensor, the interaction between the receptor material and surface of the sensor with detection function (hereinbelow, simply referred to as the sensor surface) is important, and it is desired to have a stable binding state. For such reasons, it is necessary to perform the fixing of the receptor material under strictly controlled conditions. However, it is not easy to attain the optimized conditions. Furthermore, there is a problem in that the environment for measurement by the sensor is limited depending on the substance used for coating, e.g., a water soluble polymer cannot be used for measurement in water.

Regarding the sensor selectivity, it can be designed over a broad range including those with high specificity like an antigen-antibody reaction and those with broad-range selectivity like a polymer capable of adsorbing relatively various types of a sample depending on the substance used for coating. On the other hand, because there is no clear guideline set for the sensitivity, designing based on a clear guideline is not currently possible. Recently, regarding a sensor of the type by which stress applied on a surface is detected, it has been reported that physical parameters like membrane thickness or Young's modulus of a receptor material have a great influence as described in Non Patent Literatures 1 and 2. Specifically, in the case of Young's modulus being constant, there is a tendency that the sensitivity increases until the membrane thickness reaches a certain value and the sensitivity decreases thereafter. Based on this, for a molecular self-assembled monolayer, DNA/RNA, protein, or an antigen/antibody, increasing the membrane thickness is impossible per se, and thus it is not easy to achieve the improvement of sensitivity. In the case of a polymer, it is possible to increase the membrane thickness, but there is a problem related to solubility or weather resistance as described above. In view of the background described above, although there is a guideline for control·optimization of the sensitivity and selectivity of limited types of a sensor, the optimum substance for simultaneously satisfying them is not known yet. Thus, the discovery and demonstration of the substance are anticipated.

SUMMARY OF INVENTION

Technical Problem

An object of the present invention is to provide, by using a "porous material" or a "particulate material" which has not been used as a receptor layer material until now, a receptor layer having controlled sensitivity and selectivity and high durability that cannot be achieved with a material of a related art, and a method for producing it.

Solution to Problem

According to one aspect of the present invention, provided is a sensor, wherein a sensor body of the type for detecting a physical parameter is coated with a porous or particulate material, and a sample molecule is detected based on a change in the physical parameter caused by adsorption of a sample molecule by the porous or particulate material.

Herein, the porous or particulate material may consist of an inorganic material.

The inorganic material may be silica.

The porous or particulate material may be a porous material with an average pore diameter of 1 mm or less.

The porous or particulate material may be a porous material with an average pore diameter of 0.1 nm or more and 500 nm or less.

The silica may be mesoporous silica.

The porous material or particulate material may be selected from a group consisting of an inorganic material, an organic material, an inorganic-organic hybrid material, a metal organic framework, a material with a self-assembled surfactant micelle incorporated in its structure, a material of plastic with a fiber dispersed therein, a carbon material, and a biomaterial.

The inorganic material may be one or more materials selected from a group consisting of oxide, nitride, sulfide, metal, and gold, or an inorganic matter containing a composite of a plurality of materials selected from the group at any ratio, the organic material may be an organic matter having, in the structure, a polymerizable functional group as a main chain and a substituent group in a side chain, the inorganic-organic hybrid material may be selected from a group consisting of an inorganic-organic hybrid which a composite of an inorganic material and an organic material at any ratio, the metal organic framework may be selected from a group consisting of the HKUST, IRMOF, MOF, ZIF, UIO, and MIL families of compounds, the material with a self-assembled surfactant micelle incorporated in the structure may be selected from a group consisting of a material with a cationic surfactant incorporated in silica structure and a material with a block copolymer incorporated in a metal skeleton, the material of plastic with a fiber dispersed therein may be fiber reinforced plastic, the carbon material may be a material with a skeleton of an $sp^2$ carbon atom element, and the biomaterial may be a material selected from a peptide, a protein, an enzyme, a sugar, a lipid, and a protein, or a composite of a material selected from a peptide, a protein, an enzyme, a sugar, a lipid, and a protein and the above inorganic material.

The composite in at least onet of the inorganic material and the inorganic-organic hybrid material may be of a configuration selected from a group consisting of a configuration of a heterogeneous binding in a manner of a Janus particle shape, a core-shell configuration, and a configuration in which a plurality of one type of particles are dispersed within the other type of particle.

The organic material may be selected from a group consisting of polystyrene, polymethyl methacrylate, polydivinyl benzene, polyisopropyl acrylamide, porphyrin, a compound with a substituent group introduced to a porphyrin ring, and a porphyrin-metal complex compound having a transition metal.

The surface of the porous or particulate material may be modified with one or a plurality of kinds of a surface modifying groups.

At least one of the surface modifying groups may adsorb the sample molecule.

A first surface modifying group among the plurality of kinds of surface modifying groups may be a hydrophobic surface modifying group, and a second surface modifying group among the plurality of kinds of surface modifying groups that is different from the first surface modifying group may be a hydrophilic surface modifying group which is shorter than the first surface modifying group, thereby causing a surface of the receptor layer to be macroscopically hydrophobic but microscopically hydrophilic.

The second surface modifying group may be an aminopropyl group and the first surface modifying group may be an alkyl group which has a longer chain length than the aminopropyl group.

A plurality of kinds of materials may be repeatedly present on a surface of the porous or particulate material, and each of the plurality of kinds of materials may be modified by a surface modifying group of a different type.

The plurality of kinds of materials may be at least titania and silica.

The porous or particulate material may be a nanoparticle.

The physical parameter may be one or more selected from surface stress, stress, force, surface tension, pressure, mass, elasticity, Young's modulus, Poisson's ratio, resonance frequency, frequency, volume, thickness, viscosity, density, magnetic force, magnetic charge, magnetic field, magnetic flux, magnetic flux density, electric resistance, electricity amount, permittivity, electric power, electric field, electric charge, electric current, voltage, potential, mobility, electrostatic energy, capacitance, inductance, reactance, susceptance, admittance, impedance, conductance, Plasmon, refractivity, luminosity, and temperature.

The sensor body may be a surface stress sensor or QCM.

The porous material may be synthesized in situ on a surface of the sensor body of the type for detecting the physical parameter.

According to another aspect of the present invention, an in-liquid gas sensor is provided, comprising a sensor, and a membrane covering the sensor, the membrane allowing permeation of at least part of gas molecules but not a liquid molecule, wherein a void is formed between the sensor surface of the sensor and the membrane.

The membrane may be a hollow fiber membrane or a semi-permeable membrane.

A means for applying negative pressure to the void may further be provided.

Advantageous Effects of Invention

According to the present invention, it is possible to achieve simultaneously the sensitivity, selectivity, and durability, which cannot be achieved by a receptor material of a related art, of a sensor of the type for detecting surface stress or other various physical parameters. Accordingly, measurement of gas or liquid can be carried out under various temperature and solvent conditions. Furthermore, coating with a porous material or a particulate material can be easily carried out, and no special reaction conditions, apparatus, or the like are required therefor.

DESCRIPTION OF EMBODIMENTS

Figure 1:
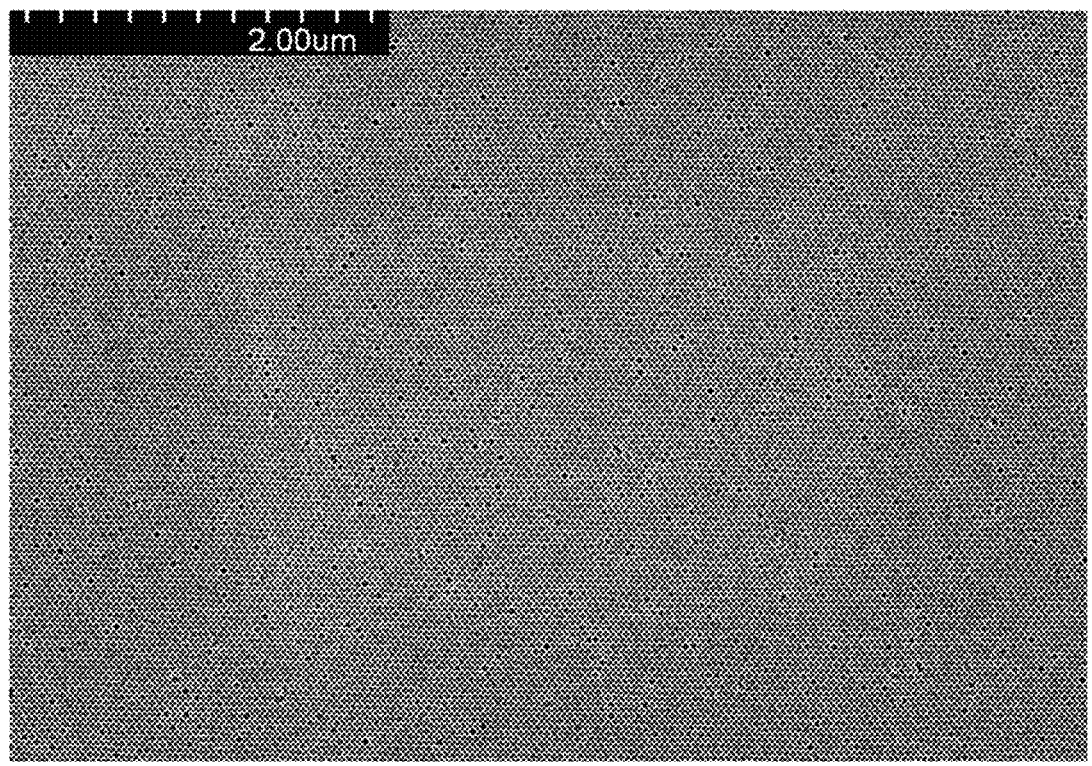
FIG. 1 is a scanning type electron microscope (SEM) image of a mesoporous silica thin membrane (average micropore diameter of 35 nm) as a typical porous material with which a sensor is coated.

Provided by the present invention is a sensor having a receptor layer which is obtained by directly coating the body of the sensor with a porous material or a particulate material (hereinbelow, the porous material and particulate material may simply referred to as the receptor material when they are collectively described), the body of the sensor being of the type for detecting surface stress, stress, force, surface tension, pressure, mass, elasticity, Young's modulus, Poisson's ratio, resonance frequency, frequency, volume, thickness, viscosity, density, magnetic force, magnetic charge, magnetic field, magnetic flux, magnetic flux density, electric resistance, electricity amount, permittivity, electric power, electric field, electric charge, electric current, voltage, potential, mobility, electrostatic energy, capacitance, inductance, reactance, susceptance, admittance, impedance, conductance, Plasmon, refractivity, luminosity, temperature, and other various physical parameters. According to this sensor, a sample molecule is adsorbed on the receptor layer and a change in physical parameters caused by the adsorption is detected by the sensor body. Thus, the sensor body which can be used in the present invention is not particularly limited in terms of structure, operation, or the like as long as a material as a detection subject is adsorbed on the receptor layer which is obtained by coating the surface with a receptor material and the change in the receptor layer, which occurs in accordance with the adsorption, is detected by it. For example, for a case in which a surface stress sensor is used, a material as a detection sample is adsorbed on the receptor layer with which the sensor surface is coated, and by detecting a change in stress occurring in the receptor layer as caused by adsorption, an output signal from the surface stress sensor is obtained. Furthermore, as a body of a sensor of another type, for a case of using QCM as a mass sensor for detecting a slight change in mass by taking advantage of a property that resonance frequency varies depending on the mass of a material which is adsorbed on an electrode surface of a quartz oscillator, by detecting a change in mass occurring in accordance with adsorption of a material as a detection subject on the receptor layer with which the surface is coated, an output signal is obtained. It should be noted that, as described herein, the term "adsorption" is used in the broadest sense to include not only the physical adsorption but also the adsorption based on chemical bonding or biochemical action.

[Receptor Layer of Porous Material]

The porous material used for a receptor layer may have any size, shape, composition, and structure. As for the composition, an inorganic material like silicon oxide may be used, and thus it is possible to use a material with high durability.

Although it is not limited thereto, examples of the inorganic material may include those having oxide, nitride, sulfide, metal, or the like as a main component, and various alloys. Furthermore, it may be a material in which the above materials are present, in any ratio, as a composite. Examples of the mode of composite may include a mode having non-uniform binding in Janus particle shape, a mode having core-shell shape, and a mode in which two or more (fine) particles are dispersed in another particle.

In addition to the above, a porous material having any metal or metal oxide can be used. In the case of a metal, an electrochemical method (e.g., electrodeposition method or the like) may be used. In the case of a metal oxide, a sol-gel method may be used, but it is not at all limited thereto. Furthermore, according to surface modification of a porous material, its chemical properties may be changed. In the present invention, if necessary, any kind of surface modification can be carried out for a porous material. For example, to have a hydrophilic or hydrophobic surface of a porous material, the surface may be modified with an amino group, an alkyl group, or the like. In addition, although it is not intended to be limited thereto, the surface modification can be carried out by using, in addition to an aminopropyl group, an octadecyl group, a silane coupling agent, a molecule having a thiol group, and phosphonic acid, various polymers or a biomolecule.

Furthermore, it is not intended to limit the porous material to an inorganic material, and other than the inorganic material, an organic material, an inorganic-organic hybrid material, a metal organic framework, a material with a self-assembled surfactant micelle incorporated in the structure, a fiber-reinforced plastic material having fiber comprising glass or carbon dispersed in plastic, a carbon material, and a biomaterial like a component derived from a living body are acceptable and components of the material do not matter. Non-limiting examples of the materials of such types may include, as an organic material, those having, in the structure, a polymerizable functional group like a double bond as a main functionality and various substituent groups in a side chain. Specific examples thereof may include polystyrene, polymethyl methacrylate, polydivinyl benzene, and polyisopropyl acrylamide. It is possible to use a porphyrin, which is an organic compound having a porphyrin ring structure. It is also possible to use a porphyrin compound having a substituent group introduced to a porphyrin ring or a complex compound having a transition metal (e.g., tin, cobalt, chrome, manganese, iron, copper, ruthenium, zinc, silver, and platinum). It is also possible to use an inorganic-organic hybrid in which the above inorganic material and organic material are combined in any ratio. Examples of the mode of composite may include, like the composite of an inorganic material, a mode having non-uniform binding in Janus particle shape, a mode having core-shell shape, and a mode in which two or more (fine) particles are dispersed in another particle. In addition, a metal organic framework (MOF) in which any metal element and organic compound form a periodic structure can be also used. Specific examples of MOF include HKUST-1, IRMOF (IRMOF-1 or the like), MOF (MOF-5 or the like), ZIF (ZIF-7, ZIF-8, ZIF-71 or the like), UIO (UIO-66 or the like), and MIL (MIL-101 or the like), in which the abbreviations or serial numbers may vary depending on the type of a metal element or the type of a substituent group binding to the organic compound. As for the MOF, any of the above is acceptable. Furthermore, specific examples of a material with a self-assembled surfactant micelle incorporated in the structure may include a material having a cationic surfactant included in silica structure and a material having a block copolymer included in a metal skeleton. Furthermore, specific examples of a material having a fiber consisting of glass or carbon dispersed in plastic may include those referred to as glass fiber reinforced plastic or carbon fiber reinforced plastic. The carbon material can be a group of materials which have $sp^2$ carbon atom element as a skeleton such as graphene or graphite, carbon nanotube, or fullerene, and it may be also an oxidized product thereof or those having chemical modification like substituent introduction. Examples of the biomaterial may include a peptide, a protein, a sugar, and a lipid, and an enzyme basically made of a protein is also included. Other than those, a composite of an inorganic material like hydroxyapatite and a protein like collagen is also included in which the latter is adsorbed on a surface of the former, for example.

It is also possible to perform enhancement or addition of a function like enhancing the sensitivity or enhancing the selectivity of a material to be detected based on suitable surface modification by binding a functional group on the surface of the porous material.

Furthermore, the average pore diameter of porous material is 0.1 nm (when it is desired to exhibit the sieving function related to detection of a very small molecule (which will be described later), it is 0.05 nm) to 1 mm. The upper limit of the pore diameter is preferably 100 μm. More preferably, it is 10 μm, even more preferably 1 μm, and still even more preferably 500 nm. Specifically, if a porous material having pore diameter at nanometer level is used as a receptor material, the micropore size can be easily controlled at 1 nm to 500 nm or so, but it is not limited thereto. By changing the molecular size of a surfactant, a block copolymer or the like that are used for the production process, the micropore size can be adjusted to any level. Furthermore, in the case of a macro-sized pore region (pore size of 100 nm or more), it is possible to use colloidal beads or the like.

Regarding the structure, it is possible to control a random porous structure as well as an orderly structure (specifically, hexagonal structure, lamellar structure, cubic structure, or the like).

Furthermore, the type of surface stress sensor which is coated with the above porous material is not particularly limited, and any kind may be used. For example, a membrane type surface stress sensor or a cantilever sensor may be preferably used.

Furthermore, for coating a sensor surface with the above porous material, raw material of a desired porous material is placed on the sensor surface by inkjet, spray, or dip methods and the porous material can be formed on the surface and the surface is coated with the material according to in situ synthesis. Alternatively, it is possible to use any other method in which a thin layer, powder, or the like of previously prepared porous material is adhered or sprayed on a sensor surface to form a coating.

It is also possible to insert another layer like a layer for improving adhesiveness, for example, between the surface of the body of the surface stress sensor and a receptor layer of a porous material. It is also possible to prepare the receptor layer to have a layer structure. Such constitution may contribute to an improvement of sensitivity, for example.

Furthermore, the surface stress sensor coated with the above porous material may be used for measurement in any environment including gas, liquid, vacuum, or the like.

Because a porous material has a very large specific area, if a porous material is used for a receptor layer, the area in which a material as a measurement subject can adsorb increases accordingly, and the effective surface stress applied to the surface stress sensor element is also increased. Furthermore, because the porous material has less rigidity compared to a material having no pores, the rigidity of the detection area of a surface stress sensor, from which a measurement signal is generated according to mechanical deformation caused by surface stress application, can be suppressed at a low level. Accordingly, it becomes possible to obtain a high output signal intensity. Furthermore, the surface stress sensor is basically to detect mechanical deformation and the detecting surface is formed on an element like a membrane or thin film which is easily deformed by slight force. However, according to the present invention, even when a receptor layer comprising a material which is rigid or brittle in bulk state is formed on such easily deformable member, it is unlikely to have any breakage or peeling. In addition, although it is not intended to be limited thereto, many inorganic substances are large rigid bodies which are not considered to be useful for a receptor layer in a related art, but which can be used for the surface stress sensor of the present invention. Accordingly, the selection range of materials that can be used as a receptor layer is broad.

Furthermore, specific effects are exhibited when the pore diameter of a porous material is very small. For example, as the molecule or cluster of a material which is adsorbed by the receptor layer has a constant size which depends on the type of material, by having the porous material function as a sieve according to adjustment of a pore diameter of a porous receptor layer, the selectivity for a desired material can be improved. Herein, since gas molecules often have low molecular weight, when the porous material is allowed to function as a sieve, it is necessary to have basically a pore diameter of 1 nm or less if optimization for such small-sized molecules is desired. By having the pore diameter set to be controllable to 0.05 nm or 0.1 nm, high selectivity for a broad range of molecules can be achieved in the molecule detection using the above sieving function.

[Receptor Layer of Particulate Material]

When a particulate material is used as a receptor material of the present invention, the general explanations and specific examples that are described in the first paragraph of the first section of [Receptor layer of porous material] are also applied. Furthermore, the particulate material may have any kind of size, shape, composition, or structure. Regarding the size, because the intermolecular force is high compared to gravity or the like when the particle size is 1 mm or less, stronger adhesive force is yielded, and therefore preferable. More preferably, it is 100 µm or less, even more preferably 1 µm or less, and still even more preferably 100 nm or less. In any case, the particle size does not matter as long as binding to a surface of a sensor body is maintained by a certain interaction. However, from the viewpoint of one aspect, it is important that the particle is not easily released from the surface of the sensor body. From the viewpoint of other aspect, as the material as a detection subject is adsorbed, if the particulate material with which a sensor surface is coated is released, a change in physical parameters occurring at the time of release may be detected.

In general, as the analysis results are shown in Non Patent Literature 3, for example, the nanoparticles have a tendency of not being easily released after they are adsorbed on the surface. As such, when nanoparticles are used as a particulate material, there are many cases in which a treatment for enhancing the adhesive force is not required, although it may vary depending on the property of the surface of the sensor body, use environment, or specifications required for the sensor. On the other hand, if the particle size is large, it is often desirable to have a binding formed between the particles and a surface of a sensor body based on chemical modification or the like.

The particle shape may be either isotropic or anisotropic. Examples of the material for forming the particle may include an element like metal, a compound like oxide and sulfide, a polymer, an inorganic-organic hybrid, and a biomaterial like protein. The structure of the particle may be a dense structure, a loose structure like a porous or hollow structure, or a core shell type structure. Furthermore, on the surface of a particulate material, any surface modifying group may be suitably fixed depending on the material as a detection subject or the like. Specifically, in addition to a silane coupling agent, a molecule with a thiol group, phosphonic acid, or the like, may be combined with a polymer or a biomolecule.

Furthermore, the particulate material may be synthesized by any method. Specifically, it includes a precipitation reaction in a homogeneous solution, a reaction in a pseudo-homogeneous system using emulsion, a reaction in the gas phase using spray drying or thermolysis, and a solid phase reaction like ball milling, and it is not particularly limited thereby.

Examples of the sensor body which is coated with a receptor layer of a particulate material include a surface stress sensor. The shape, material, size, or the like are not particularly limited, and any subject may be used. For example, a thin beam type body supported at one point or more than one points may be used. Other than that, those with various shapes like a thin beam type body, a membrane body, or the like that are supported at two or more points including a double-fixed beam may be employed.

Furthermore, in addition to the surface stress sensor, by using a sensor which uses an oscillator such as QCM or cantilever, or surface plasmon resonance (SPR), the same effect as above can be achieved after coating with a receptor of particulate material.

Methods for coating the sensor surface with a receptor of a particulate material include dip coating, spray coating, spin coating, inkjet coating, casting, and coating using a doctor blade, and are not particularly limited.

Furthermore, when the particulate material used as a receptor layer can efficiently adsorb by itself a target sample molecule, such a particulate material can be used directly. Alternatively, by modifying the particulate material with a specific surface modifying group, the target sample molecule may be adsorbed, the adsorption efficiency is improved, or the selectivity for the material to be adsorbed is increased, thus an improvement of the detection performance can be achieved. Furthermore, the modification with a surface modifying group can be also carried out for the purpose which is not directly related with adsorption of a sample molecule, for example, to improve the binding between particles, adhesiveness to the substrate, durability of a sensor of particulate material, and resistance to the environment or the like. Furthermore, as described below, it is also possible to modify the surface of a particulate material such that a plurality of kinds of surface modifying group are present, in a mixed way at the nanometer level.

In a receptor layer formed by coating the sensor surface with a particulate material of the present invention, voids may be created during the process of forming the receptor layer by aggregation of the particles, among particles that form the particulate body. Because such voids work as pores, the receptor layer becomes porous in most cases. Such a receptor layer is formed by coating with the particulate material, and at the same time, it is a receptor layer which is formed of a coating with a porous body made up of particles that are aggregated. Thus, the features explained herein for a receptor layer of a porous material may also be applied in the same way to a receptor layer of a particulate material, unless apparently inappropriate. Conversely, it is to be noted that, as long as the receptor layer formed by coating with the particulate material is poroux's, it has the features that are explained for the receptor layer coated with a porous material. Furthermore, it is evident that a receptor layer formed by coating with a particulate material comprising a porous material has characteristics of both the receptor layer of a porous material and receptor layer of a particulate material, as long as the voids on the surface of the receptor layer are not clogged.

As an example of an exceptional case in which the receptor layer constituting a particulate material is not porous, there may be a case in which, if the diameter of the particle for forming the particulate body is excessively small, the pores between the particles that are left after the aggregation process are smaller than the size of a molecule which is subject to detection so that practically it does not function as a porous material for the detection subject, a case in which the particles have a flat plate shape with excessively high aspect ratio and most of the surface of the receptor layer is covered with the flat plate so that the pores formed inside do not remain open to the surface of the receptor layer, a case in which the surface of a sensor body is coated with the particles only at very low density so that a large void is created among the particles and a void, which cannot be described as a "pore", is generated, and a case in which, for some reasons, it is impossible to reach the internal pores from the surface of a receptor layer even when the pores are present inside the receptor layer.

Hereinbelow, the features achievable by a sensor which has, as a receptor, a coating layer of a porous material or a particulate material of the present invention are exemplified.

(1) When the sensor sensitivity depends on the membrane thickness of a receptor layer, by controlling the membrane thickness according to lamination of a porous material or a particulate material by any method, the sensitivity can be controlled.

(2) It is possible to control the area in which a measurement subject is adsorbed. Specifically, the specific surface area can be controlled by changing the pore diameter of the porous material or the size of the particulate material to be laminated.

(3) It is possible to ensure the space (route) which is required for the measurement subject to access the inside of a receptor layer. Specifically, when a porous material is used, the route is provided by the pores. When a particulate material is used, the size of the voids formed among the particulate materials can be controlled by modifying the size of particulate material to be laminated.

(4) Because a porous material or a particulate material is used as a receptor layer, a great deal of freedom is allowed other than the material used for the receptor layer. Specifically, depending on the measurement subject, it is possible to select a suitable composition of porous material or particulate material, type of surface modifying group, or a combination of a plurality of kinds of porous material or particulate material.

(5) Depending on the measurement environment, it is possible to select a porous material or a particulate material having the required hydrophilicity/hydrophobicity, heat resistance, chemical resistance, or the like. Namely, compared to a configuration in which a surface of the sensor is coated with a uniform layer of a conventional technique, a material with broader properties can be selected by adhering a porous material or a particulate material.

With regard to the above (5), in the case of a polymer which is commonly used in a related art, for example, various kinds of polymer are present. Thus, a suitable polymer can be selected depending on the measurement environment. However, since there is a great variation in terms of suitable solvent or coating conditions for each polymer, the optimum conditions needs to be determined in each case. On the other hand, in the case of the porous material or particulate material like nanoparticles of the present invention, various properties can be realized only with one kind of host material by allowing different modifying groups to coexist on the surface of the material.

The modifying group can be suitably selected; for example, in the examples of the receptor layer of a particulate material described below, silica-titania hybrid particles are used as a particle, and the surface is modified with an alkyl group and an amino group. The important aspect of the configuration of the nanoparticle surface which is produced in Example 2 is that the longest modifying group present on the surface of nanoparticles is an alkyl group so that it has macroscopically a hydrophobic property. On the other hand, microscopically, an amino group is present and it also contributes to the adsorption. Namely, even when the amino group is replaced with another modifying group, or a further separate modifying group is attached in addition to the amino group, the macroscopic properties remain the same as long as the alkyl-group modification density is not extremely low or a chain longer than the alkyl groups is not attached. Thus, it is not necessary to determine the coating conditions for each case. For the reasons described above, it becomes possible to determine and select, roughly independently from each other, the selection of a sample molecule for adsorption by a receptor molecule and the properties of a receptor layer.

Furthermore, the modifying group for the receptor layer of a porous material is basically the same as those described above. In the case of a porous material, if there is a case in which the inner surface area (i.e., surface of pores that are present inside of the material) is significantly larger than the outer surface area (i.e., macroscopic surface area of the material), some circumstances are different. For example, in the porous membrane of Example 1 explained below, a membrane with sponge-like structure is fixed on the sensor surface. The sponge-like structure part has dominantly large inner surface area while the outer surface area is relatively small. As a result, in such a case, the modifying groups are present in a relatively large amount in the inside so that the modifying groups exposed to the outer surface are deficient, and thus there is a possibility of having a reduced effect of the modifying groups. For example, because it is considered that the macroscopic hydrophobic property described above is determined by the outer surface instead of the inside of the pores, there is a possibility that the aforementioned effect may not be sufficiently exhibited depending on the coating density of modifying groups.

(6) Since various inorganic porous materials or inorganic particles may be used as a material of the receptor layer, the receptor layer can be imparted with high heat resistance. Accordingly, at high temperature, various materials can be detected with high sensitivity by using various types of sensor including a surface stress sensor. For example, in the case of performing solder reflow or performing the measurement in molten solder or the nearby area, it is required to have a sensor that is capable of operating at high temperatures of around 250° C. As an example, although the modifying groups are an organic substance, the MSS coated with silica-titania hybrid particulate material, which has been modified with an aminopropyl group and an octadecyl group, as shown in Example 2 can endure relatively high temperatures and functions sufficiently even at 250° C., because silica-titania hybrid material is used as the particle. If no modifying groups are used for the receptor layer, even higher heat resistance can be easily achieved. Though Example 2 is an example in which the receptor layer is made of a particulate material, the same shall apply for the receptor layer made of a porous material.

EXAMPLES

Hereinbelow, the present invention is explained in more detail based on Examples, but the present invention is not limited to those Examples.

<Example 1> MSS Having Receptor Layer of Porous Material Formed by Coating with Mesoporous Silica Using Spray Coating Hereinbelow, by taking the membrane type surface stress sensor (MSS) as an example of a surface stress sensor, the effect obtained by coating with, as a porous material, a mesoporous material which has a pore diameter of several nanometers to several tens of nanometers as a receptor is explained.

In the present example, a mesoporous silica thin membrane was used as a porous material. The production method is well known, but brief explanations are as follows. First, for forming a mesoporous silica thin membrane, a precursor solution comprising an organic template (surfactant/block copolymer), silica source, and an organic solvent is prepared, and the precursor is applied on a substrate. As the solvent evaporates, the surfactant/block copolymer is self-assembled, and a silica skeleton is formed around it. The template is removed by calcination, and desired mesoporous silica is obtained. The pore diameter of porous silica can be controlled based on the size of the organic template (surfactant/block copolymer), and it can be controlled to 2 nm to 100 nm or so. In the present example, mesoporous silica with an average pore diameter of 35 nm of which SEM image is shown in FIG. 1 was used.

Figure 2:
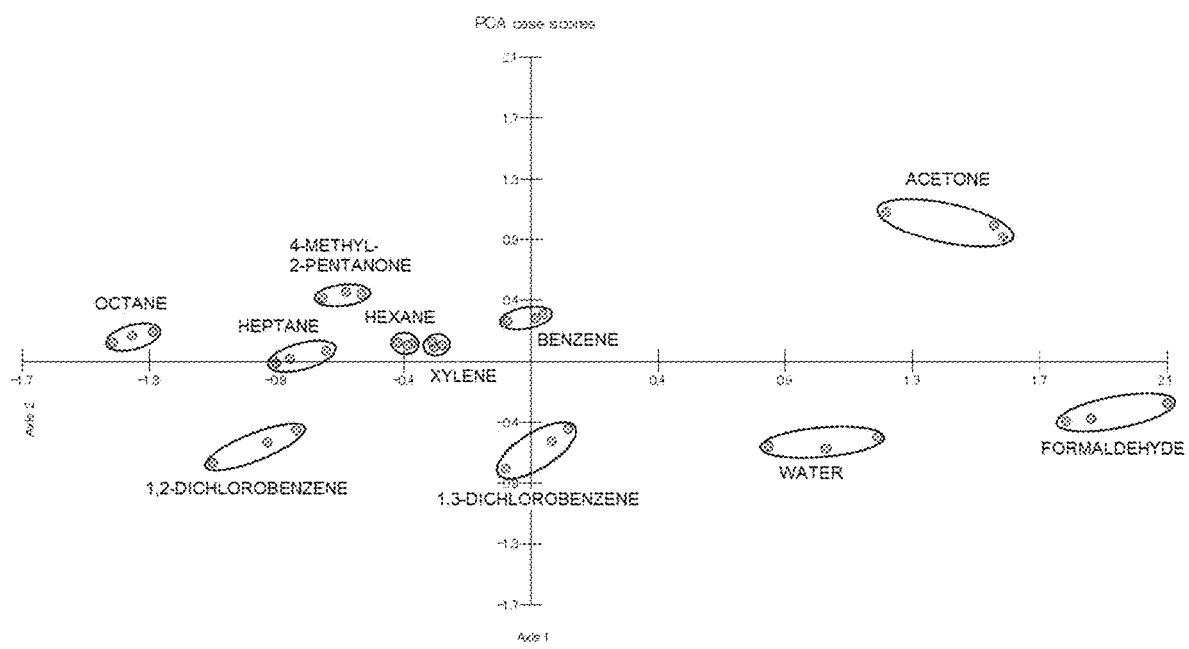
FIG. 2 is a drawing illustrating an example of gas identifying measurement by using a membrane type surface stress sensor which has a porous receptor layer coated with a porous material, and represents a result of analyzing the main component of a sensor output for various gases.
Figure 4:
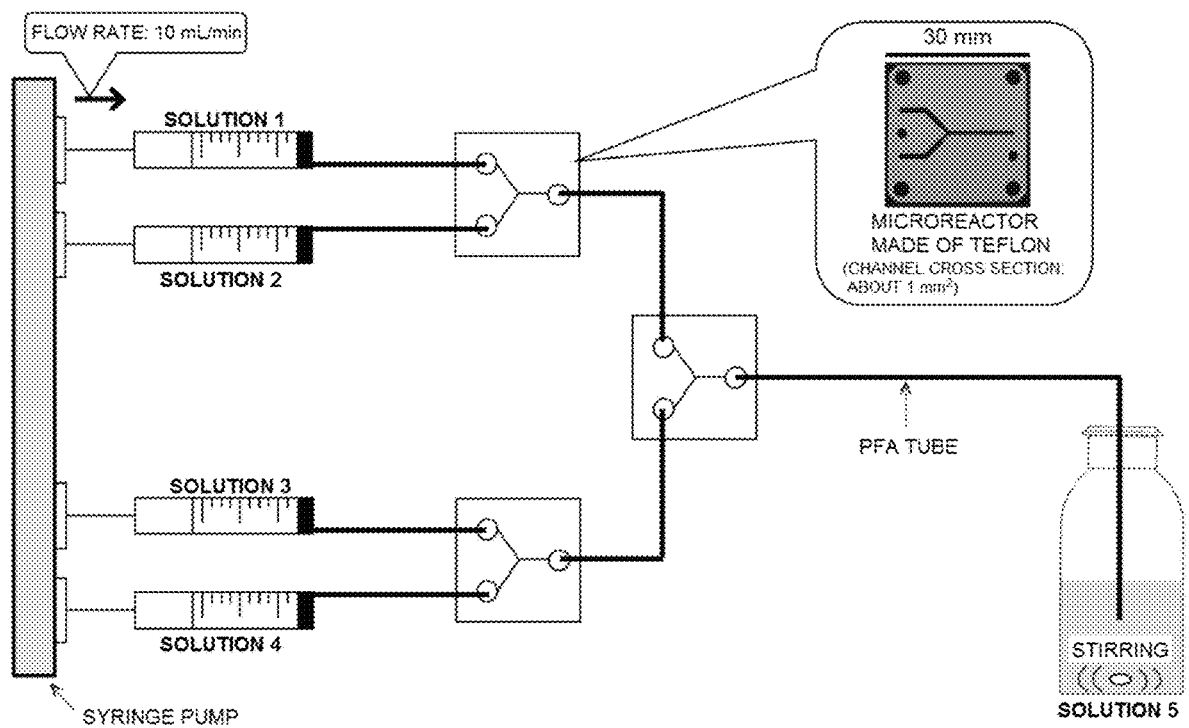
FIG. 4 is a drawing illustrating a typical configuration of a device which is used for synthesis of the particulate material of Example 2.

FIG. 2 shows a result which is obtained by main component analysis of the measurement result of various gases by using an MSS with a receptor layer of a porous material, which has been formed by spray coating with mesoporous silica of which SEM image is shown in FIG. 1. For the measurement, to a 2 ml vial bottle in which about 1 ml of a solution corresponding to various gases described in FIG. 4 has been added is connected with a Teflon (registered trademark) tube for gas introduction and, by flowing, as a carrier gas, dry nitrogen gas at a flow rate of 100 ml/min, with the saturated vapor in the head space of the vial, a chamber containing a sensor chip coated with mesoporous silica was introduced with the gas for 10 seconds. After that, dry nitrogen gas was introduced for 10 seconds. This process was repeated 3 times. From the attenuation curve which is obtained by purging the gas molecule adsorbed onto mesoporous silica by using dry nitrogen gas, a plurality of signal values were extracted at constant intervals. Then, using those values, the main component analysis was performed. It was found that, even when the measurement was carried out using saturated vapor of an organic solvent which can dissolve materials including polymer, various gas components can be identified. It was also found that such a result can similarly be measured without being affected much by the repeated measurement.

Figure 3:
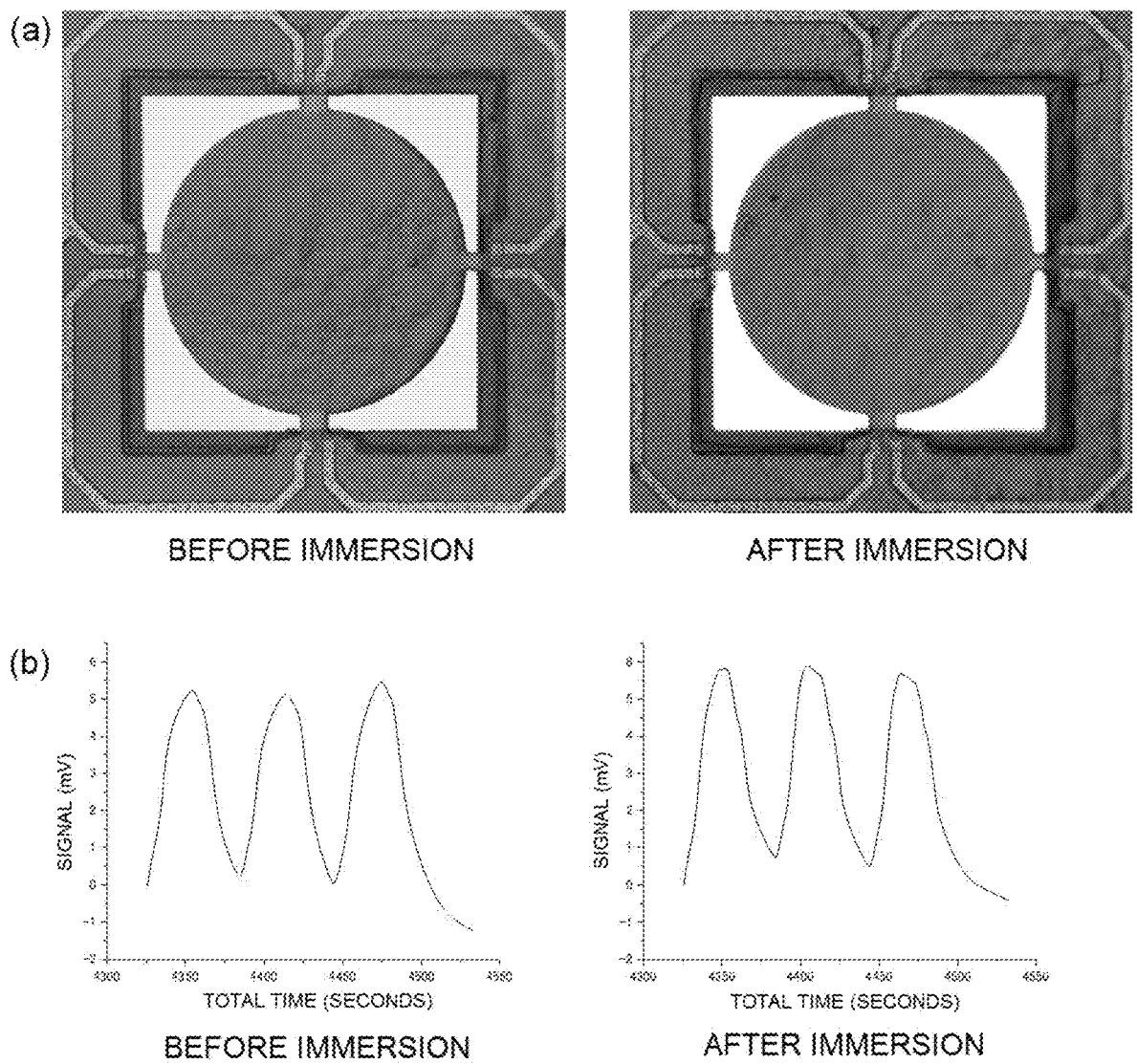
FIG. 3(a) is an optical microscope image of a membrane type surface stress sensor which has a porous receptor layer coated with a porous material, either before (left) or after (right) the immersion in liquid water and ethanol
FIG. 3(b) is an example of signal obtained by measuring octane vapor, either before (left) or after (right) the immersion of a membrane type surface stress sensor which has a porous receptor layer coated with a porous material in liquid water and ethanol.

FIG. 3(a) and FIG. 3(b) indicate the determination of a change in membrane shape and signal when the aforementioned MSS coated with mesoporous silica is immersed in liquid water and ethanol. More specifically, the signal before immersion was obtained, at the same conditions as described above, by flowing alternately saturated octane vapor and dry nitrogen, each with a flow rate of 100 ml/minute for 30 seconds. Water was applied for 1 minute or so to the inside of the closed chamber in which the sensor chip is placed, and ethanol was subsequently applied for 1 minute or so. All of those operations were performed at room temperature. After that, the measurement was carried out again at the same conditions as those before the immersion, and a signal was obtained. Accordingly, it was confirmed that the outer appearance of the membrane shape on the MSS hardly changes before and after immersion and immersion in those liquids have almost no effect on the signal of the measurement result.

Thus, it was found that, when a porous material is used as a receptor layer, the membrane shape or signal is hardly affected by gas at high concentrations or immersion in liquid solvent, and repeated measurement can be made. Such high durability is basically derived from the use of an inorganic material as the porous material used in the above experiment. When this experimental test is evaluated in the context of the present invention, it is confirmed by the experiment that sufficiently high durability is exhibited even when the prepared receptor layer is porous and any negative influence caused by porosity is hardly observed.

<Example 2> MSS Coated with Silica-Titania Hybrid Particulate Material which is Modified with Aminopropyl Group and Octadecyl Group Hereinbelow, explanations are given for an example in which a receptor layer is produced by using the aforementioned particulate material and the measurement is made by using it. In general, the particulate material prepared by the following method has a diameter of several nanometers to several hundreds of nanometers. Thus, in the present example, the particulate material which is used is described as "nanoparticles". However, it is evident that the particulate material of the present invention is not limited to diameters at the nanometer level.

Figure 5:
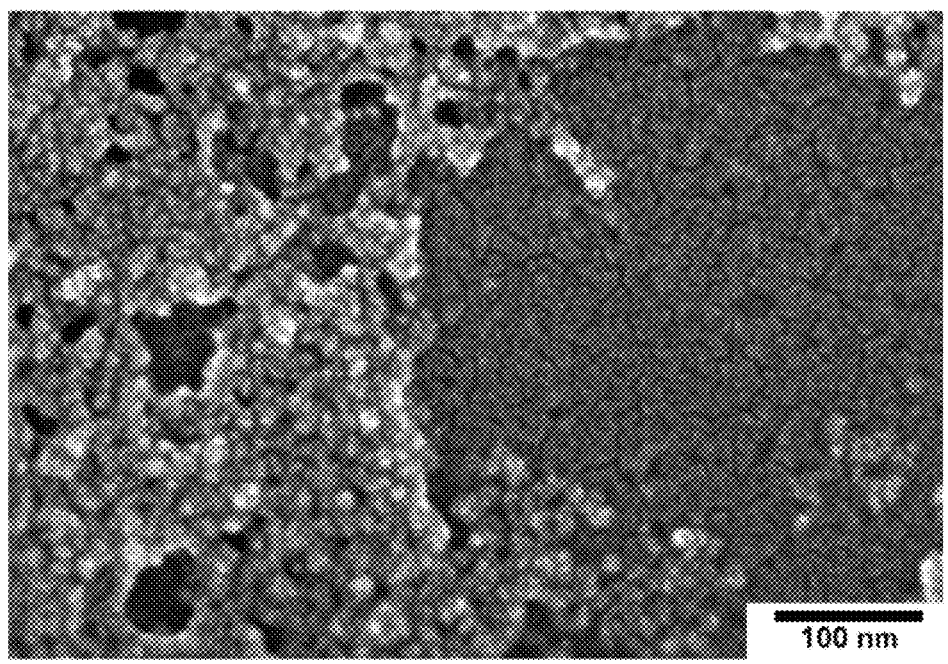
FIG. 5 is a SEM image of the particulate material prepared in Example 2.

The nanoparticles were synthesized by co-hydrolysis and condensed polymerization reaction of aminopropyl triethoxysilane (APTES) and titanium tetraisopropoxide (TTIP) in ammoniac basic aqueous solution of isopropanol (IPA) in which octadecylamine (ODA) is dissolved. The synthesis reaction was performed by using a Teflon (registered trademark) microreactor having a Y-shaped flow path with micrometer size (FIG. 4) (Non Patent Literature 4). The precursor solution was prepared from the following four solutions—solution 1: APTES/IPA, solution 2: $H_2O$/IPA/ammonia, solution 3: TTIP/IPA, and solution 4: $H_2O$/IPA. Solution 1 to solution 4 were prepared to have the same volume. The precursor solution was transported simultaneously at constant rate by using a syringe pump. Each of solution 1 and solution 2, solution 3 and solution 4 was mixed in microreactors arranged in parallel, and by admixing the liquid discharged from the two reactors in another microreactor, one reaction solution was prepared. The reaction solution was discharged in precursor solution 5: ODA/$H_2O$/IPA which was prepared separately, and it was stirred at constant speed until the end of discharge. After that, by keeping it at room temperature, a dispersion of nanoparticles was obtained. The image of the nanoparticles observed by SEM is shown in FIG. 5.

By mixing the dispersion of nanoparticles with a certain amount of water, the particle concentration was adjusted to 1 g/L. After dispersing the particles by ultrasonic wave application, they were directly sprayed onto a sensor chip of the sensor body using a spray coater. As a sensor body, the piezoresistance type MSS that has a membrane type structure as described in Patent Literature 1 was used.

Figure 6:
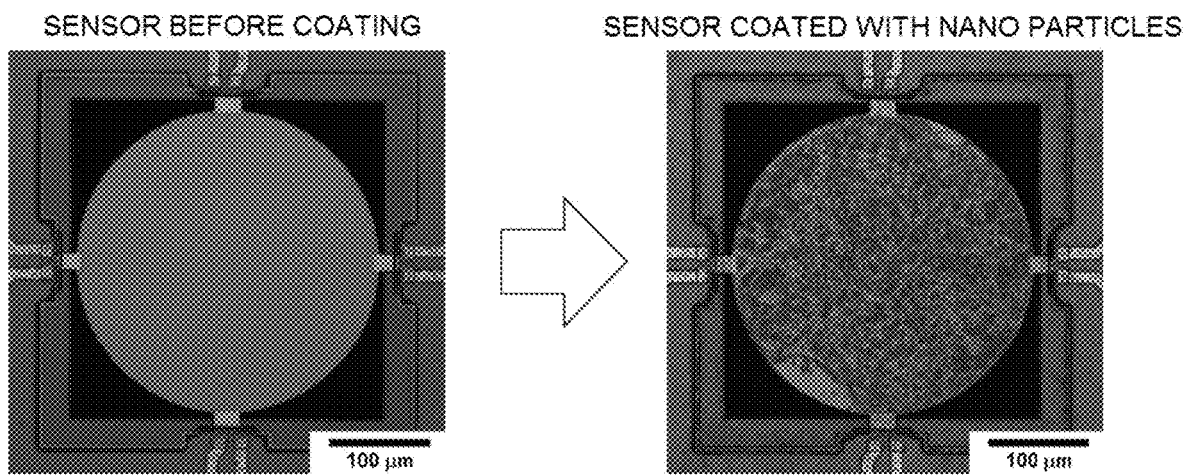
FIG. 6 is an optical microscope image of a membrane type surface stress sensor (MSS) before and after coating with the particulate material of Example 2.

The optical microscope image of the MSS after coating with the nanoparticles, which were prepared in this example, is shown in FIG. 6. Compared to the image before the coating, it was confirmed that the entire membrane structure is coated.

Figure 7:
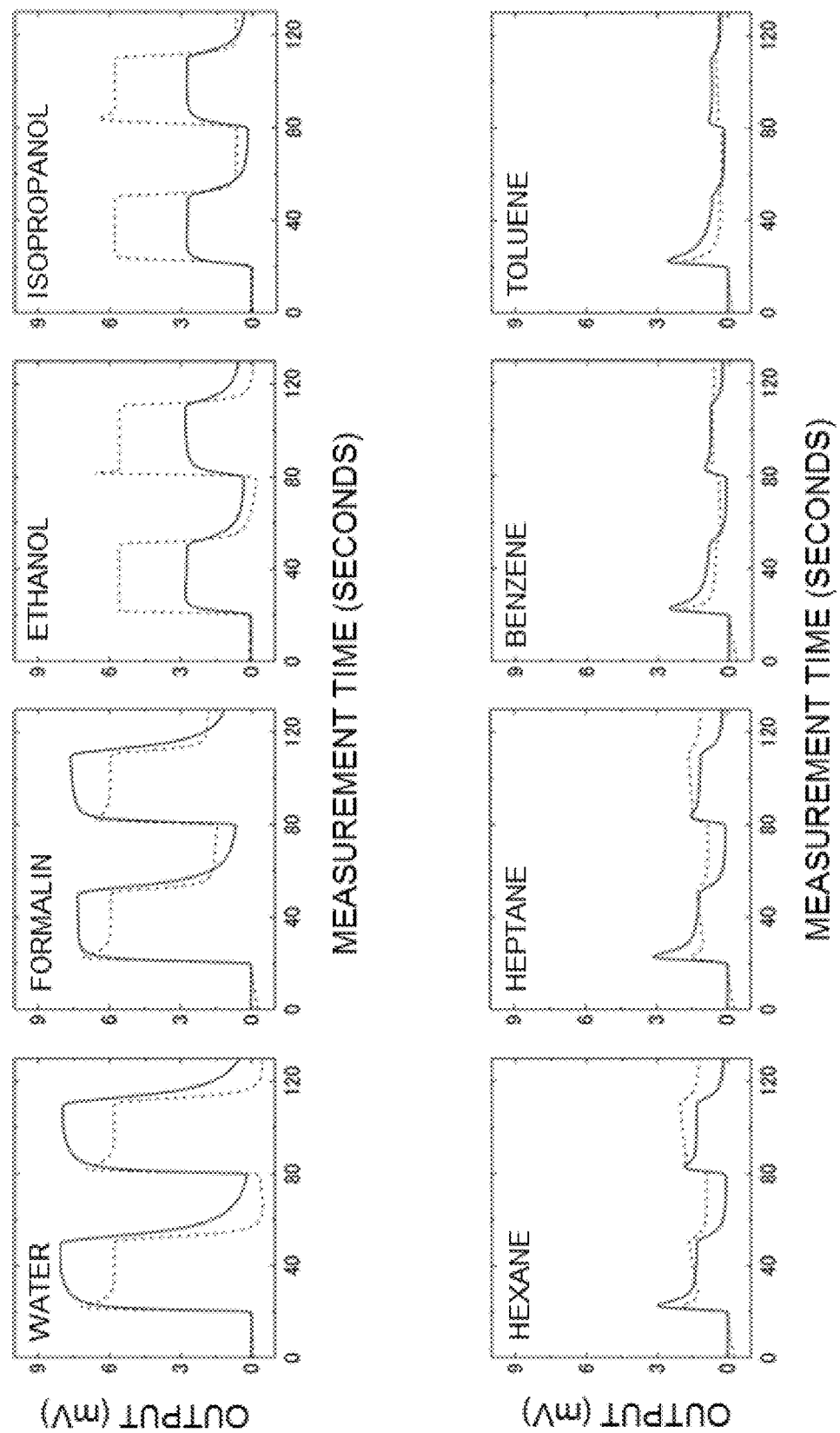
FIG. 7 is a drawing illustrating the result of measuring eight kinds of compound by using MSS coated with the particulate material of Example 2 and MSS coated with polyvinyl pyrrolidone (PVP) as a subject for comparison.

By using an MSS that has a receptor layer formed as above, measurement of water and chemical species that are either easily soluble or hardly soluble in water was performed. Specifically, each of eight kinds of chemical including water, formaldehyde (formalin), ethanol, IPA, hexane, heptane, benzene, and toluene was collected in a vial, and by flowing nitrogen gas as a carrier gas at 100 mL/min thereto, gas containing a constant amount of sample vapor was introduced to a sealed chamber containing the MSS. The result obtained by measuring each sample vapor is shown in FIG. 7. For comparison, a piezoresistance type MSS with the same structure was coated with PVP (1 g/L solution) as an example of a universal polymer using the same spray coater as above, and the measurement was carried out that yielded the results shown in FIG. 7. In case of water and formaldehyde, a signal of 7 to 8 mV or so was obtained from the MSS with the receptor layer of this Example. However, from the PVP-coated MSS used for comparison, a signal of 6 mV or so was obtained. In the case of ethanol and IPA, the signal intensity obtained from the MSS of this Example was lowered to 3 mV or so. In the case of the PVP-coated MSS, however, an output slightly lower than 6 mV was obtained. On the other hand, in the case of hexane, heptane, benzene, and toluene, i.e., compounds hardly soluble in water, a weak signal of 1 mV or so was obtained from all MSSs. Thus, when the MSS that have a receptor layer obtained by coating with nanoparticles is compared to the MSS coated with PVP only, the sensitivity for an aqueous sample was high while the sensitivity for an alcohol sample was low. In this regard, it is believed that, while PVP has in its structure a hydrophobic hydrocarbon chain and a hydrophilic substituent group (i.e., a polar group containing N and O), the nanoparticles containing a large amount of a hydrophilic aminopropyl group which is used herein adsorb a large amount of water. From the above, it was found that coating with the nanoparticles only is sufficient to have at least the same sensitivity as the universal polymer, and the selectivity can be controlled based on the type of modifying group.

Figure 8:
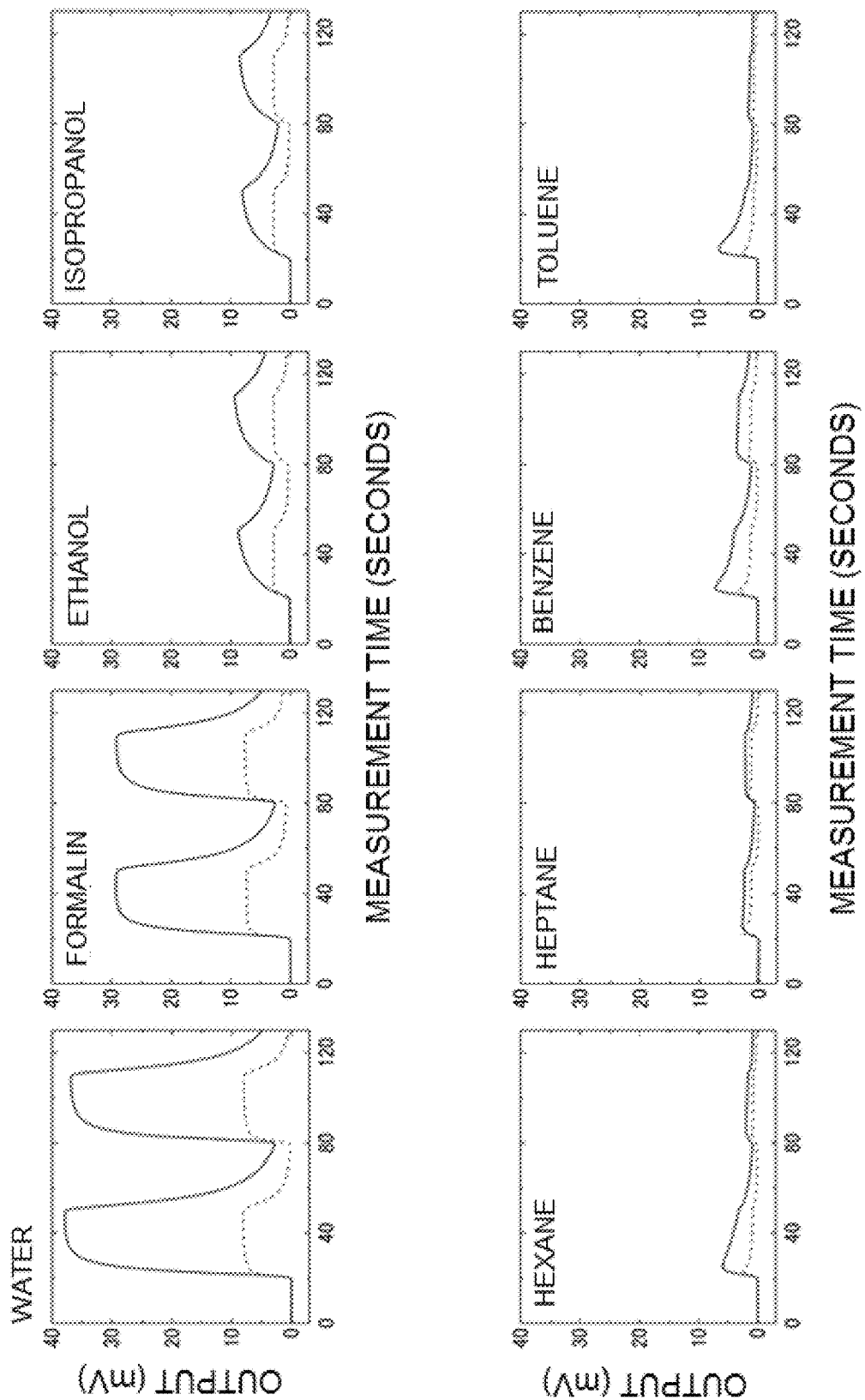
FIG. 8 is a drawing illustrating the result of measuring eight kinds of compound by using MSS coated, 5 times in a row, with the particulate material of Example 3.

<Example 3> High Sensitivity Obtained by Lamination of Nanoparticles of Silica-Titania Hybrid which are Modified with Aminopropyl Groups and Octadecyl Groups The same nanoparticles as those used in Example 2 were prepared as a dispersion with a concentration of 1 g/L, and used for coating of an MSS. Coating was continuously performed 5 times by using a spray coater, and by using the MSS with an increased membrane thickness of receptor layer, measurements were made for the eight kinds of a compound as described in Example 2. The measurement results are shown in FIG. 8.

The characteristic response trend regarding the compound which is either easily soluble or hardly soluble in water is the same as in Example 2. The absolute sensitivity value for water and the compounds easily soluble in water was increased by 5 times or so. Accordingly, it was proven that, by controlling the amount of nanoparticles in the coating, a receptor layer of nanoparticles which has any membrane thickness and enables stable measurement can be produced. It was also proven that the sensor sensitivity can be enhanced in conjunction with the increased membrane thickness.

Figure 9:
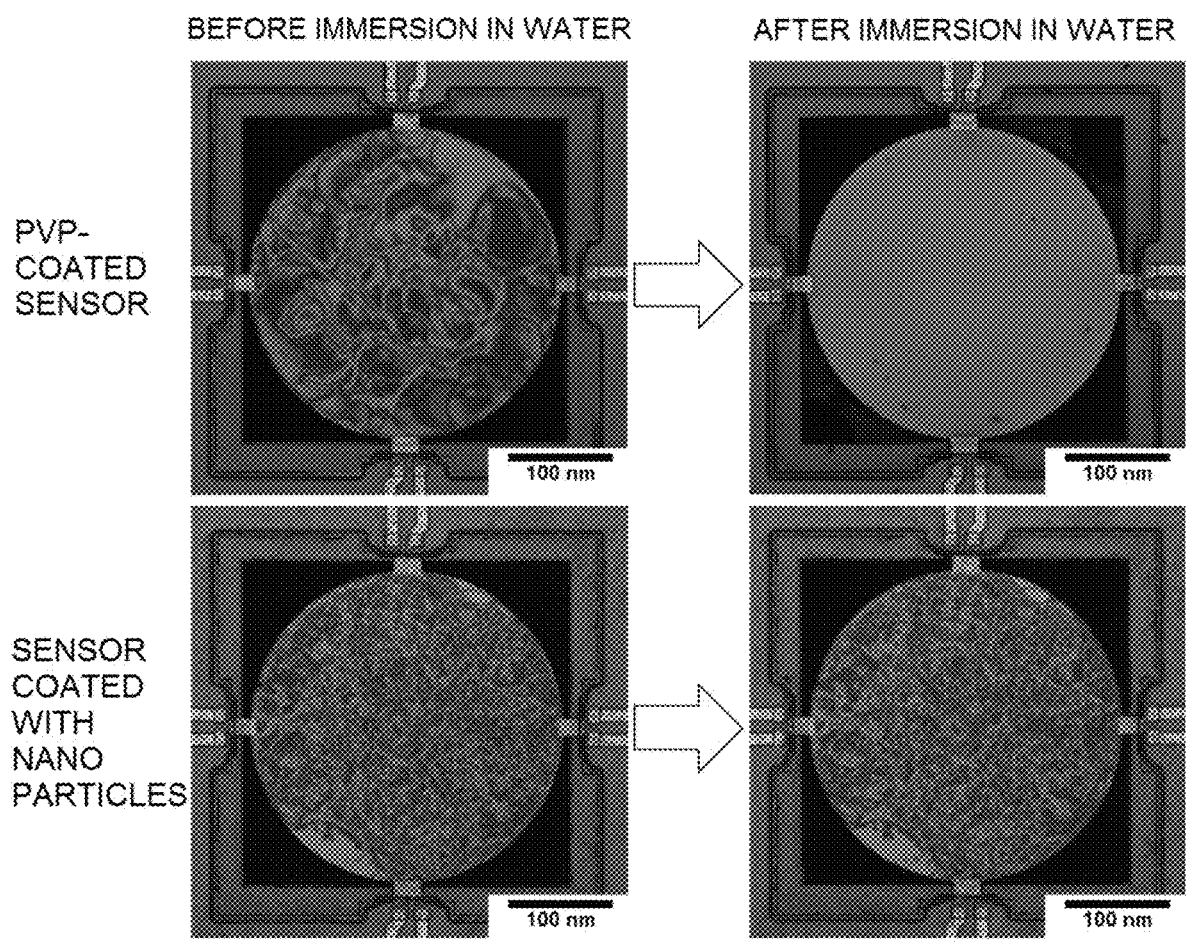
FIG. 9 is an optical microscope image of MSS coated with the particulate material of Example 4, before and after the immersion in water, and also shows, as a subject for comparison, an optical microscope image of PVP-coated MSS, before and after the immersion in water.

<Example 4> In-Water Use of MSS Having Receptor Layer Coated with Nanoparticles of Silica-Titania Hybrid which is Modified with Aminopropyl Group and Octadecyl Group The MSS that has a receptor layer coated with nanoparticles as described in Example 2 was immersed in water for a few seconds. After removing it from water followed by drying, measurements were made for the eight kinds of compound as above. First, the optical microscope image before and after immersion in water is shown in FIG. 9. As a comparison, an example of a PVP-coated MSS is also shown. In the case of PVP, it was found that PVP is completely dissolved after the immersion in water. On the other hand, in the case of the MSS coated with nanoparticles, the appearance of the MSS has not changed at all before and after the immersion and the completely intact receptor layer was confirmed at the naked eye level.

As described above, according to this Example, spraying a suspension of dispersed nanoparticles for coating the sensor body was sufficient to form a strong receptor layer of particulate material, which does not show any damage, like loss, even when it is immersed in water. Examples of the attractive forces which may occur among the particles include intermolecular forces and electrostatic forces. In the case of the intermolecular force, for example, it increases in inverse proportion to the square of the particle diameter such that stronger adhesion is obtained with smaller particles. As such, as described in the above, without performing a special treatment during adhesion or using another material for aiding adhesion like a binder during the adhesion process, once bound to the surface, the nanoparticles are strongly adhered thereto and are not easily released therefrom. However, it is evident that it does not prevent the use of other means for further enhancement of the adhesion strength.

Figure 10:
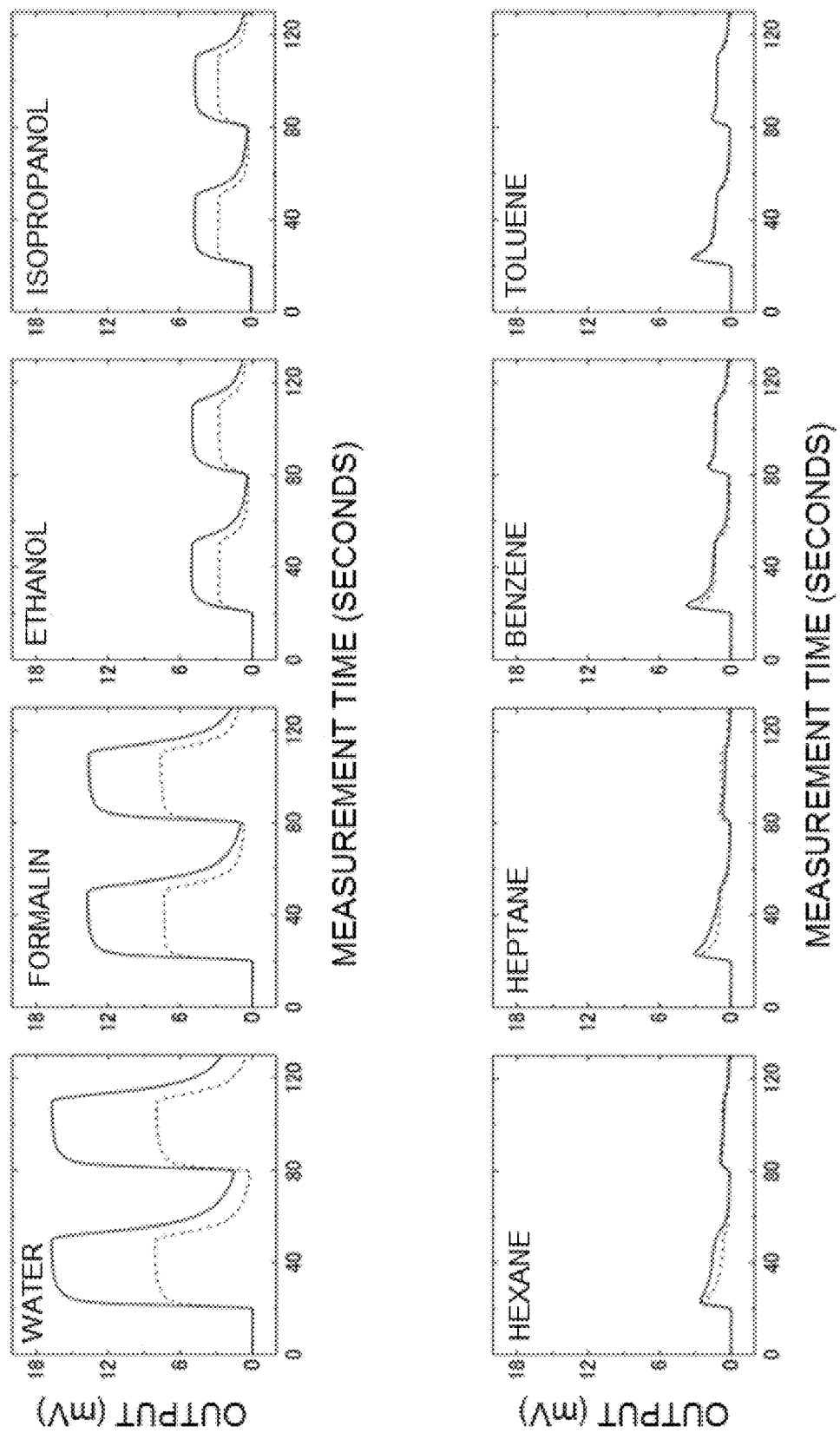
FIG. 10 is a drawing illustrating the result of measuring eight kinds of compound by using MSS coated with the particulate material of Example 4, before and after the immersion in water.
Figure 11:
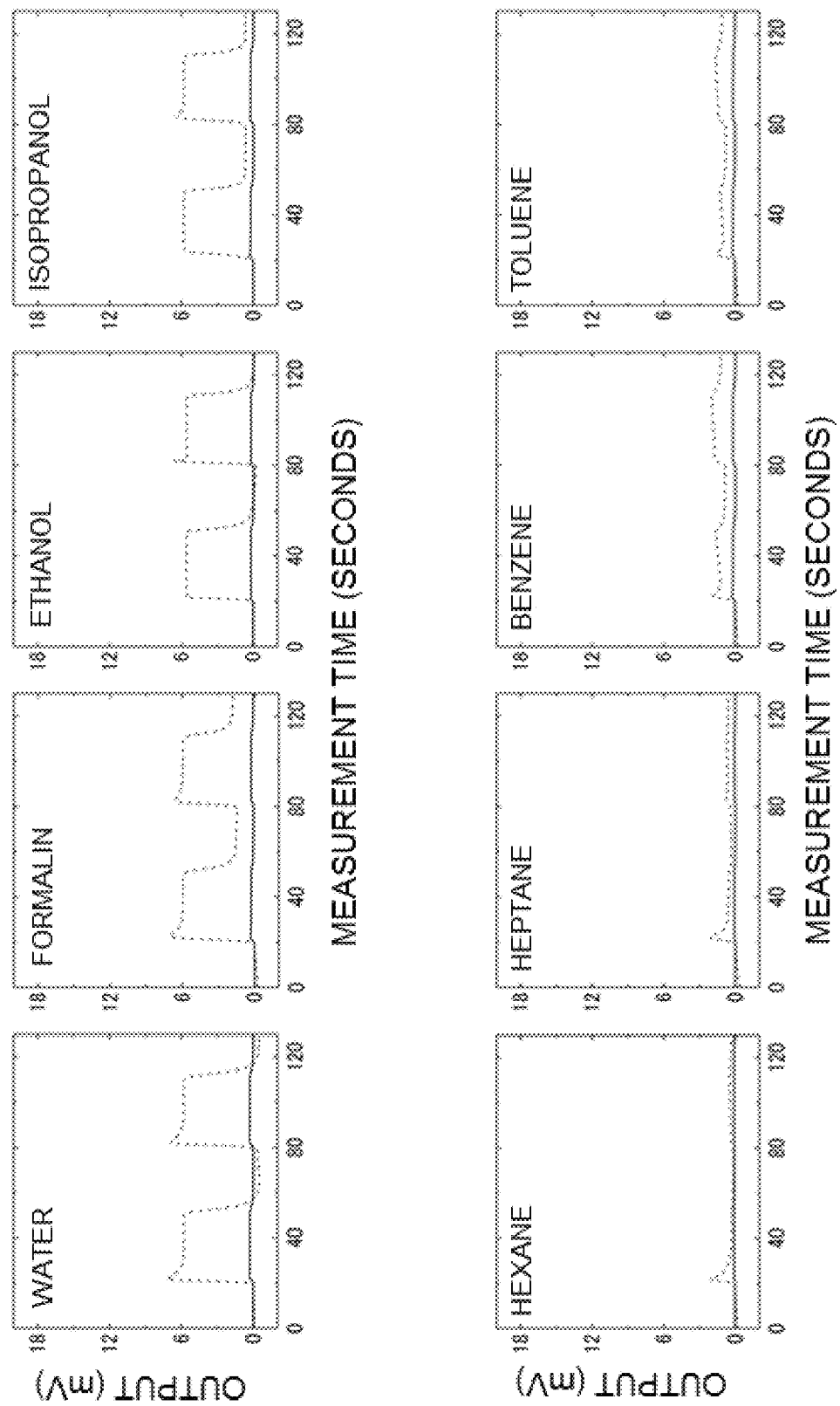
FIG. 11 is a drawing illustrating the result of measuring eight kinds of compound by using PVP-coated MSS of Example 4, before and after the immersion in water.

Furthermore, the measurement results obtained for the eight kinds of compound are shown in FIG. 10 and FIG. 11. In the case of the sensor coated with nanoparticles shown in FIG. 10, the compounds which are hardly soluble in water give the same signal before and after immersion in water. Furthermore, a sensitivity increase of about 2 times was shown from water and the compounds which are easily soluble in water. In this regard, it is believed that the excess ODA bound with the nanoparticles is removed by immersion in water so that more sample molecules can be adsorbed thereto. On the other hand, as shown in FIG. 11, in the case of the PVP-coated MSS, the PVP receptor layer is dissolved in water when it is immersed in water as can be confirmed from FIG. 9. Accordingly, the PVP hardly remains on the MSS surface such that it was almost impossible to confirm any signal from any of the compounds.

By observing the MSS chip being pulled out from water, it was found that water is completely repelled by the MSS which has a receptor layer coated with nanoparticles, indicating a hydrophobic surface. However, the adsorption characteristic showing high sensitivity toward an aqueous sample demonstrates the presence of a hydrophilic surface. It is understood that this can be a result of the cooperative action of the octadecyl group from ODA fixed on the titania surface and the aminopropyl group fixed on the silica surface. Namely, due to the presence of an octadecyl group that has a long chain length, it may be macroscopically hydrophobic. However, due to the co-presence of an aminopropyl group, microscopically there are many sites for adsorbing water, and thus the MSS is able to achieve a state in which water in the bulk state, i.e., liquid, is repelled but water vapor (in other words, water molecules dispersed in gas, but not water in the bulk state) is adsorbed. Considering that the chain length of the octadecyl group and aminopropyl group is several angstroms (Å) to 1 nm or so, it is believed that, as the MSS coated with the nanoparticles is placed in water in which molecules having affinity for amino groups are dissolved (e.g., proteins or the like), adsorption occurs such that the sample molecule is selectively adsorbed from water. Based on the above, not only the in-gas measurement but also the in-liquid measurement of which there are no previous examples, like direct measurement of the concentration of various gases in blood, can be achieved.

More specific explanations of the "in-liquid measurement" described herein are as follows. When a particle with hydrophilic and hydrophobic modifications as described just above is used, if it is assumed that both modifying groups are periodically arranged on the particle surface (or, although not periodic in a strict sense, they are alternately present at very short intervals), the hydrophilic groups and hydrophobic groups are present in turn. When water in the bulk state contacts the surface in such a state, there is a possibility of having a "pocket" like state in which air is included between neighboring hydrophobic groups. Under the arrangement state described above, because a hydrophilic group is present between hydrophobic groups so that the hydrophilic group exists in a region having this "pocket", and thus it is expected that the distance between the tip of the hydrophilic group and bulk water is less than 1 nm. As such, by adsorbing the molecules dissolved in the liquid at this pocket, it becomes possible to detect the dissolved molecules. In other words, it is possible to have a kind of in-gas measurement in the liquid. As can be seen from the above (5) regarding the "features achievable by a sensor which has, as a receptor, a coating layer of a porous material or a particulate material of the present invention", this measurement method can be basically realized with a receptor layer in which a porous material is used. However, it should be also noted that, depending on the structure of the porous material, it may not work satisfactorily.

So-called "in-liquid gas measurement" as described above can also be achieved by having a structure for encapsulating the sensor element so as to create a gas atmosphere corresponding to the above "pocket" around the sensor element by using a material which has the property of allowing permeation of gas molecules but not liquid molecules (for example, a hollow fiber membrane with a two-dimensional shape which is used for removal of gas dissolved in liquid, or a semi-permeable membrane having such property can be used). By doing so, it becomes possible for the sensor element to detect gas components that are dissolved in a liquid sample without contacting the liquid sample. In that case, as for the receptor layer for coating the sensor element, any material that can be used for measurement of a gas sample can be used in principle. For example, as confirmed by FIG. 9, a hydrophilic polymer like PVP is immediately dissolved after the immersion in water, and thus in-liquid measurement is impossible. However, by taking advantage of the "in-liquid gas measurement" principle using a hollow fiber membrane as explained herein, it is possible to have measurement in water.

Figure 14:
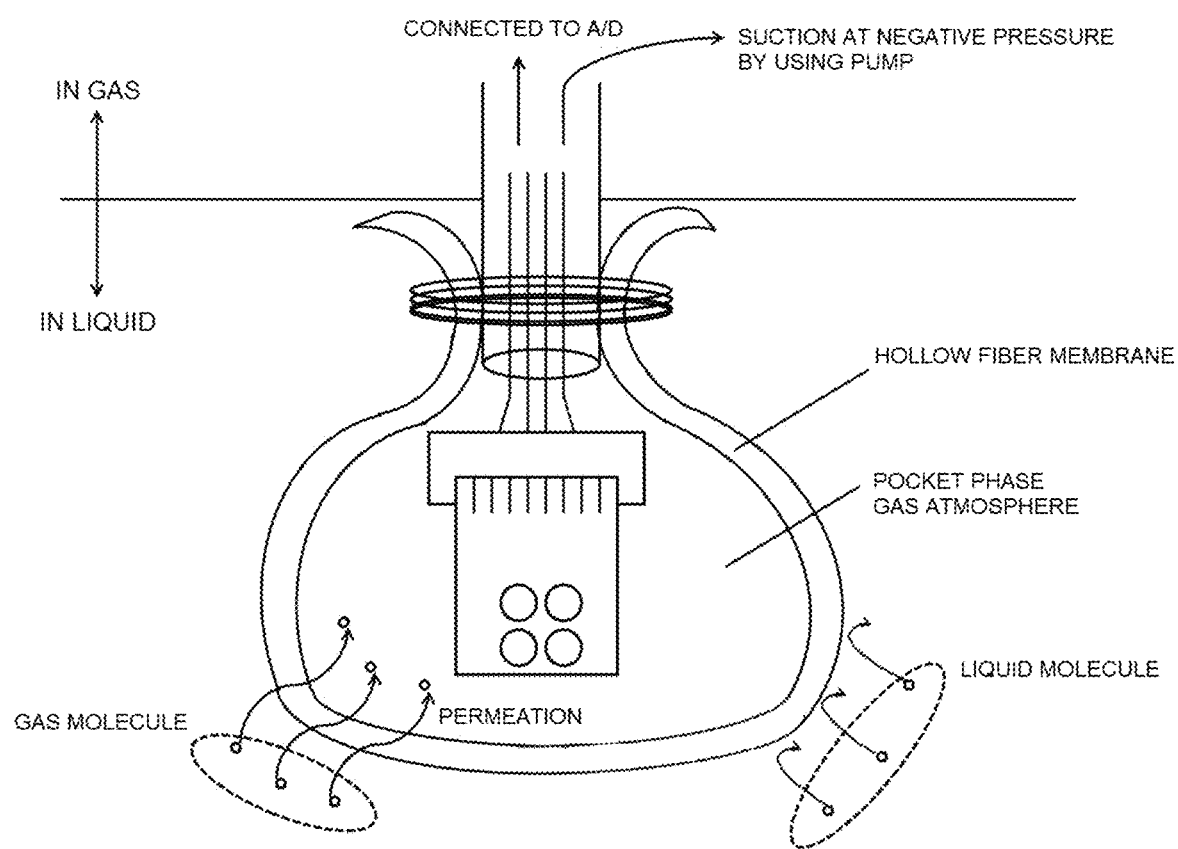
FIG. 14 is a drawing explaining a typical device for performing in-liquid gas measurement by using a membrane comprising a material which allows permeation of gas molecules but not liquid molecules.

FIG. 14 shows a conceptual drawing of a configurational example for performing in-liquid gas measurement based on encasulating a surface stress sensor within an pouch-like hollow fiber membrane. In the in-liquid gas sensor shown in FIG. 14, the MSS is used as a sensor body, and a surface stress sensor with a receptor layer adapted for the gas molecule to be measured formed on the surface is encapsulated within an pouch-like hollow fiber membrane. Furthermore, a signal line for transporting the detection signal, which comes from an electrical connector to the MSS, is drawn to the upper side as shown in the drawing and it is connected to an A/D converter of a measuring instrument not shown. Furthermore, around the bottom part of the tube for collecting the signal line, the pouch of the hollow fiber membrane is attached in a water-tight manner. Furthermore, it is configured such that negative pressure can be applied to the hollow fiber pouch via a tube. In use, it is immersed in a liquid sample while the surface pressure sensor is encapsulated within the hollow fiber membrane pouch. The hollow fiber membrane does not allow permeation of liquid molecules (e.g., water) but allows permeation of certain kinds of gas molecules depending on the composition or structure of the membrane. As such, the gas molecules dissolved in the liquid sample permeate the hollow fiber membrane and migrate to the pocket-like gas atmosphere inside the hollow fiber membrane pouch. In this state, if negative pressure is applied to the envelope via a tube, the permeation of the gas molecules can be accelerated. Furthermore, by application of negative pressure, the volume of the hollow fiber membrane envelope, i.e., volume of the pocket-like gas atmosphere, is reduced due to the pressure difference between the inside and outside. As the volume of the pocket-like gas atmosphere is reduced, the concentration of the permeated gas in the atmosphere can reach an equilibrium state within a short time.

The "in-liquid gas measurement" herein has the following characteristics when compared to a case in which a sensor element is placed right above a liquid sample and vapor of the liquid sample is measured. Because it is possible to immerse in liquid the sensor element and the entire gas atmosphere corresponding to the surrounding closed "pocket", measurement under a more stabilized environment can be made compared to an environment in which a gas atmosphere like vapor is quite unstable. Furthermore, by having negative pressure on the inside of the hollow fiber membrane, i.e., the side that has the sensor element, by suction using a separate pump or the like, impure components present in the gas atmosphere corresponding to the "pocket" can be reduced and, also, the gas molecules can be actively extracted from the liquid sample. Accordingly, measurement with higher precision can be achieved.

Furthermore, although a structure in which the whole surface stress sensor is encapsulated in a pouch-like membrane is shown in FIG. 14, it is also possible to have an in-liquid gas sensor with compact configuration by covering only the sensor surface of the surface stress sensor (or, in addition to the sensor surface, the surroundings of the sensor surface) with a membrane.

The periodic or almost periodic mixed presence of hydrophilic modifying groups and hydrophobic modifying groups on the surface of the nanoparticles of this Example is made possible due to the reason that the nanoparticles are silica-titania hybrid nanoparticles and a silica part and a titania part, to which each modifying group binds, are repeatedly present on the surface. To produce nanoparticles in which a plurality of materials are repeatedly present on a surface, it is sufficient that a plurality of alkoxides are mixed and reacted in the presence of an organic compound as shown in Example 2. Furthermore, to control the size and shape of the nanoparticles that are produced by this reaction, a flow synthetic method can be used like Example 2. The flow synthetic method is explained in Non Patent Literature 4, for example. Furthermore, also for the porous material, the periodic mixed presence of modifying groups can be similarly achieved as above.

Conditions for having a microscopically hydrophilic state include a longer chain length of the hydrophobic group on the particles (more generally, on the surface of the receptor layer), than the chain length of the hydrophilic group on particles. Accordingly, water in the bulk state is repelled by the hydrophobic groups, but individual molecules can access the hydrophilic group. It is believed that theoretically the same phenomenon can also be achieved with a smooth surface which is not coated with nanoparticles. However, coating the surface of a smooth substrate or the like with modifying groups that have opposite properties like hydrophilicity and hydrophobicity each other in close proximity so as to have the aforementioned phenomenon is practically difficult to achieve. Having opposite properties like hydrophilicity and hydrophobicity at the particle level is also advantageous in terms of easy achievement.

The activity obtained by performing modifications using a plurality of kinds of surface modifying group on a particle surface is not limited to the cooperative action of the plurality of kinds of surface modifying group as described above. For example, one of the plurality of kinds of surface modifying group may achieve enhanced detection sensitivity or selective detection based on its binding to a sample molecule, and another modifying group may increase the durability and environmental resistance of particles binding to the sensor surface based on its binding to the sample body surface.

<Example 5> Application to Sensor of Type for Detecting Different Physical Parameter (e.g., QCM)

Figure 12:
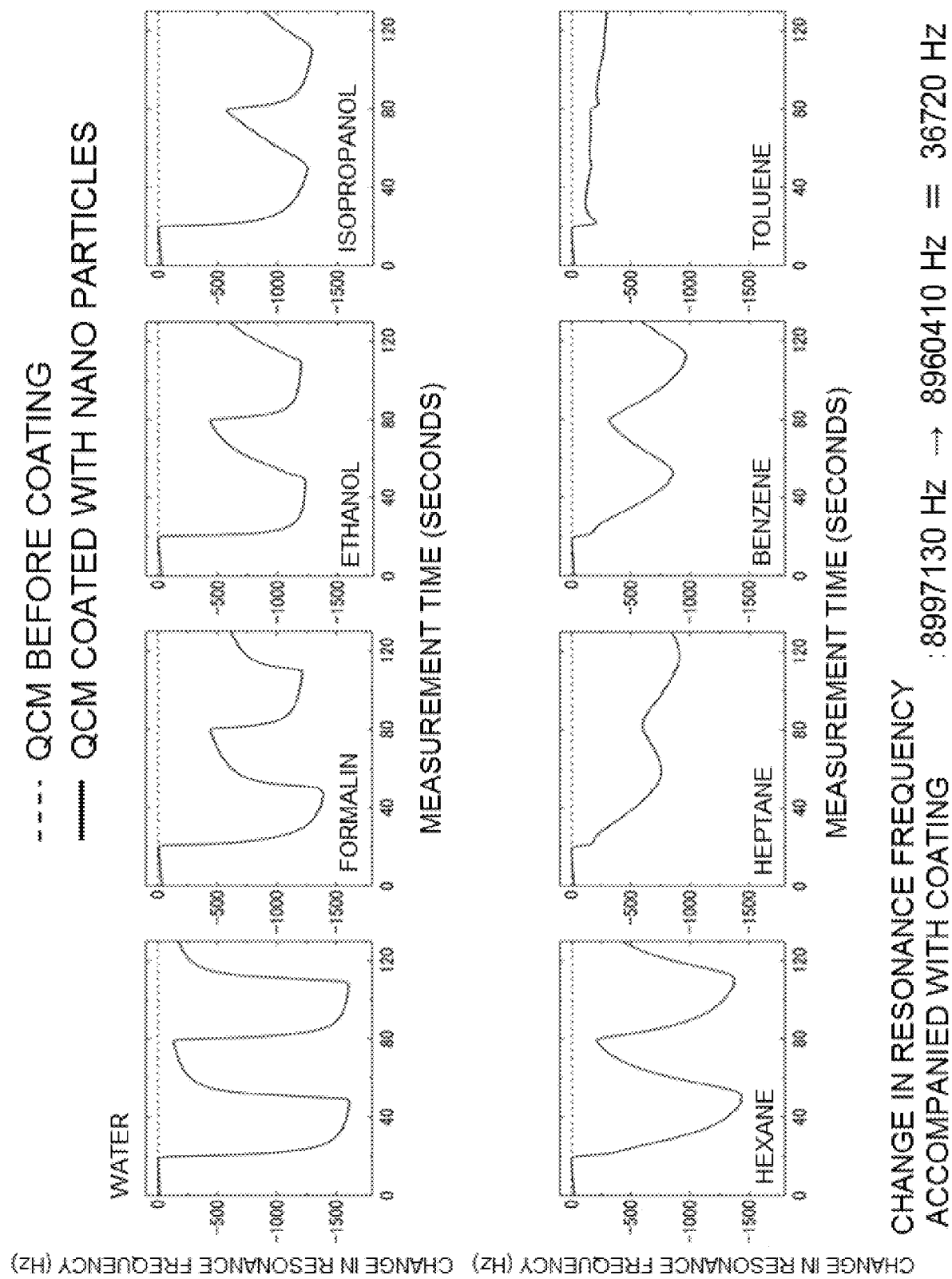
FIG. 12 is a drawing illustrating the result of measuring eight kinds of compound by using QCM coated with the particulate material of Example 5, and also illustrates, as a subject for comparison, the result of measuring eight kinds of compound by using QCM before coating with the particulate material.

In Example 5, according to the same order as Example 2, a QCM was coated with nanoparticles, and used for measurement of the eight kinds of a compound described above. Even for a case in which a QCM is used as a sensor body, the receptor layer that has a coated surface has almost the same structure as an MSS. The measurement results are shown in FIG. 12. For the all compounds, the QCM before coating with nanoparticles showed a change in resonance frequency of only 1 to 2 Hz. However, after the coating with nanoparticles, the change in resonance frequency was increased by several hundred to several thousand times. Furthermore, as there is a signal waveform which is clearly different for each compound, it was possible to determine the compound with the naked eye.

Figure 13:
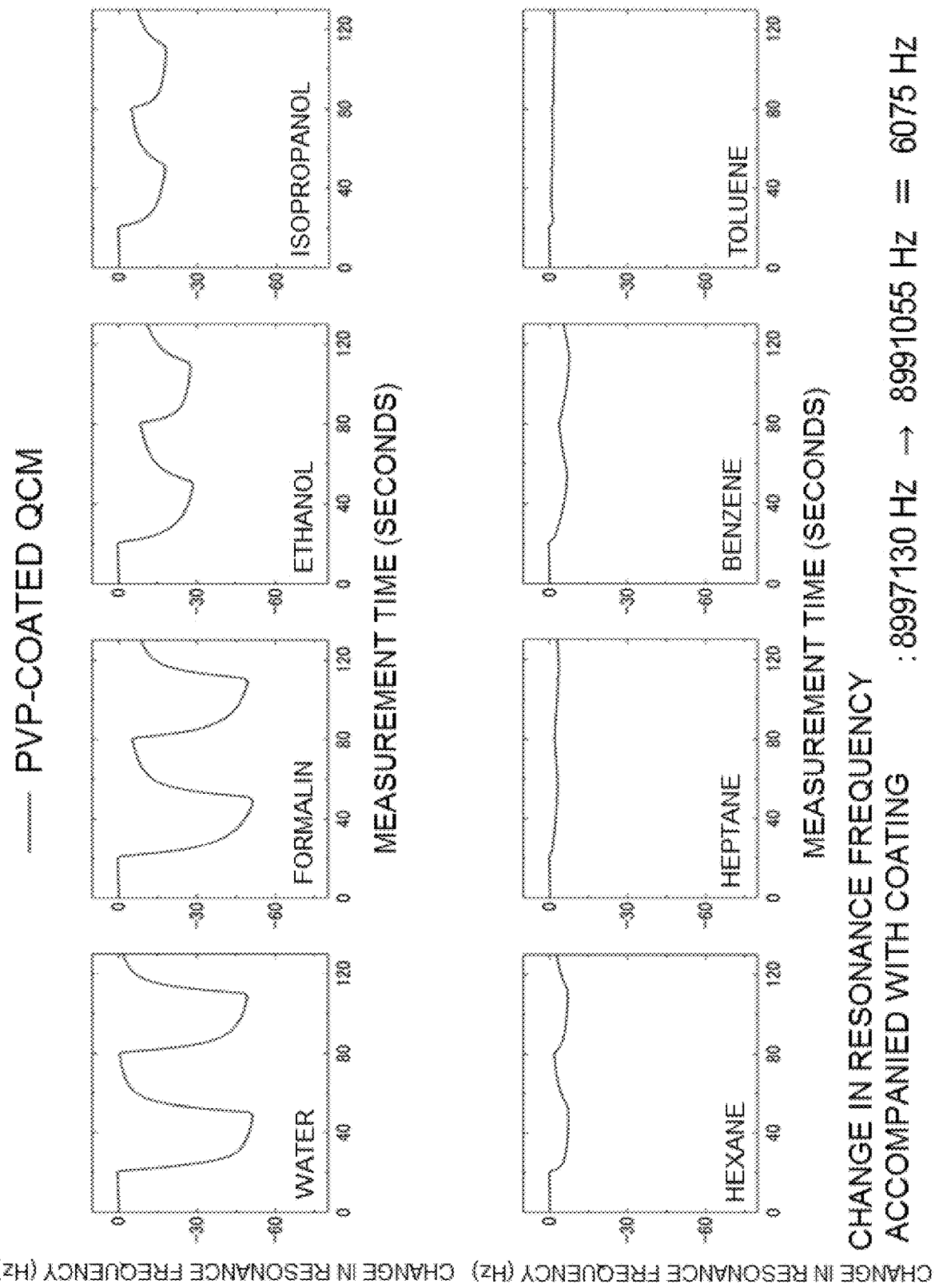
FIG. 13 is a drawing illustrating the result of measuring eight kinds of compound by using PVP-coated QCM of Example 5.

By using a PVP-coated QCM as a comparative subject, measurement of the eight kinds of compound described above was carried out. The results are shown in FIG. 13. The change in resonance frequency was as high as 50 Hz, and the smaller value was as low as several Hz. Herein, it is known that the change in resonance frequency is in an approximately proportional relationship with a change in mass occurring on the QCM. Since the resonance frequency of the QCM before coating as used herein is about 8,997,130 Hz, but it was 8,991,055 Hz after coating with PVP, the change in resonance frequency accompanied with coating was found to be about 6 kHz. On the other hand, since the resonance frequency after coating with nanoparticles was 8,960,410 Hz, the change in resonance frequency accompanied with coating was found to be about 36 kHz. Namely, the nanoparticles present on the electrode surface of the QCM are about 6 times larger than PVP in terms of mass. Based on this, it is believed that, in order to compare the measurement result of each compound obtained by using the PVP-coated QCM with the measurement result of each compound obtained by using the QCM coated with nanoparticles, the change in resonance frequency needs to be multiplied by 6 times for the former if the comparison is made for a unit mass of coated receptor material. In that case, the change in resonance frequency will be as high as 300 Hz. However, even when compared to the case of coating with nanoparticles, it is still about 6 times smaller.

According to above, it was shown that high sensitivity and high selectivity can be achieved even with coating other kinds of sensor surface with nanoparticles, and the results are significantly higher than a case in which a conventional material is used as a receptor layer. Similar results are obtained in the case of having a porous receptor layer.

Figure 15:
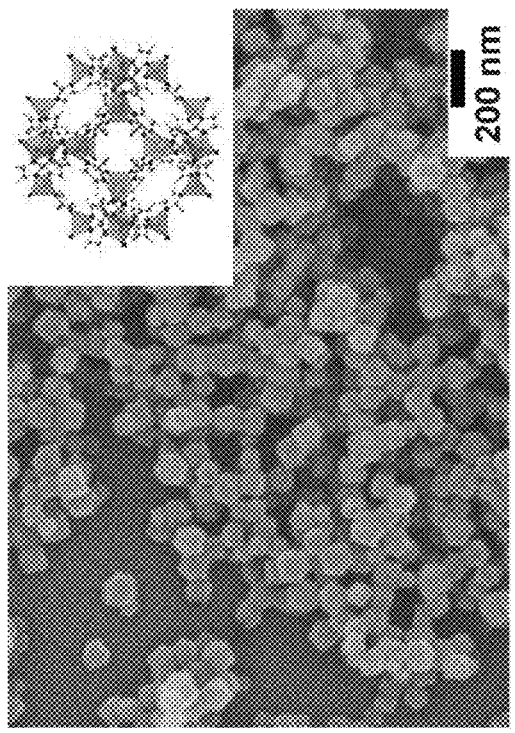
FIG. 15 is a SEM image of three kinds of metal organic framework (MOF) ZIF-7, ZIF-8, and ZIF-71 having different structure, and the upper right corner of each SEM image represents the crystal structure of corresponding MOF.
Figure 15:
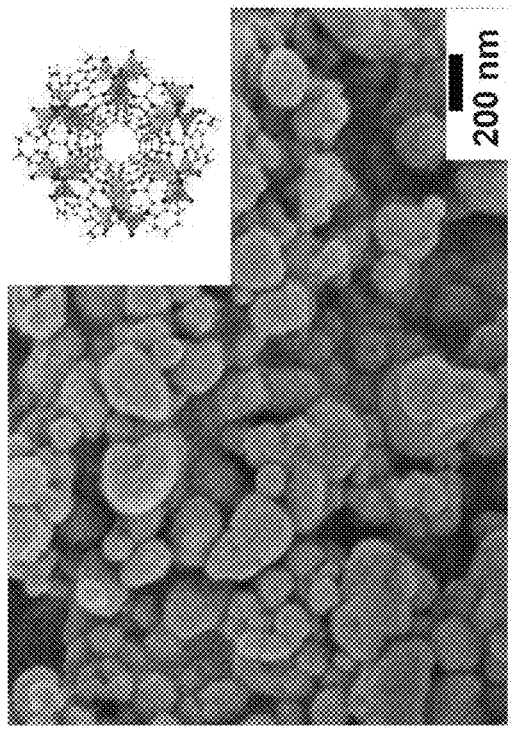
Figure 15:
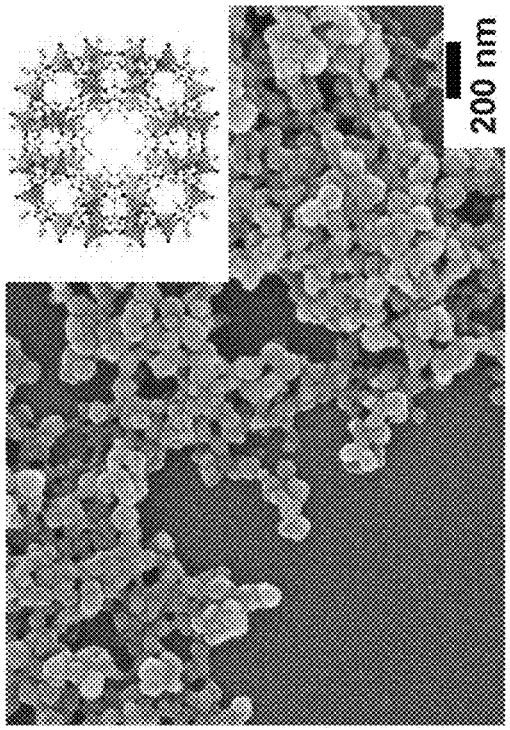
Figure 16A:
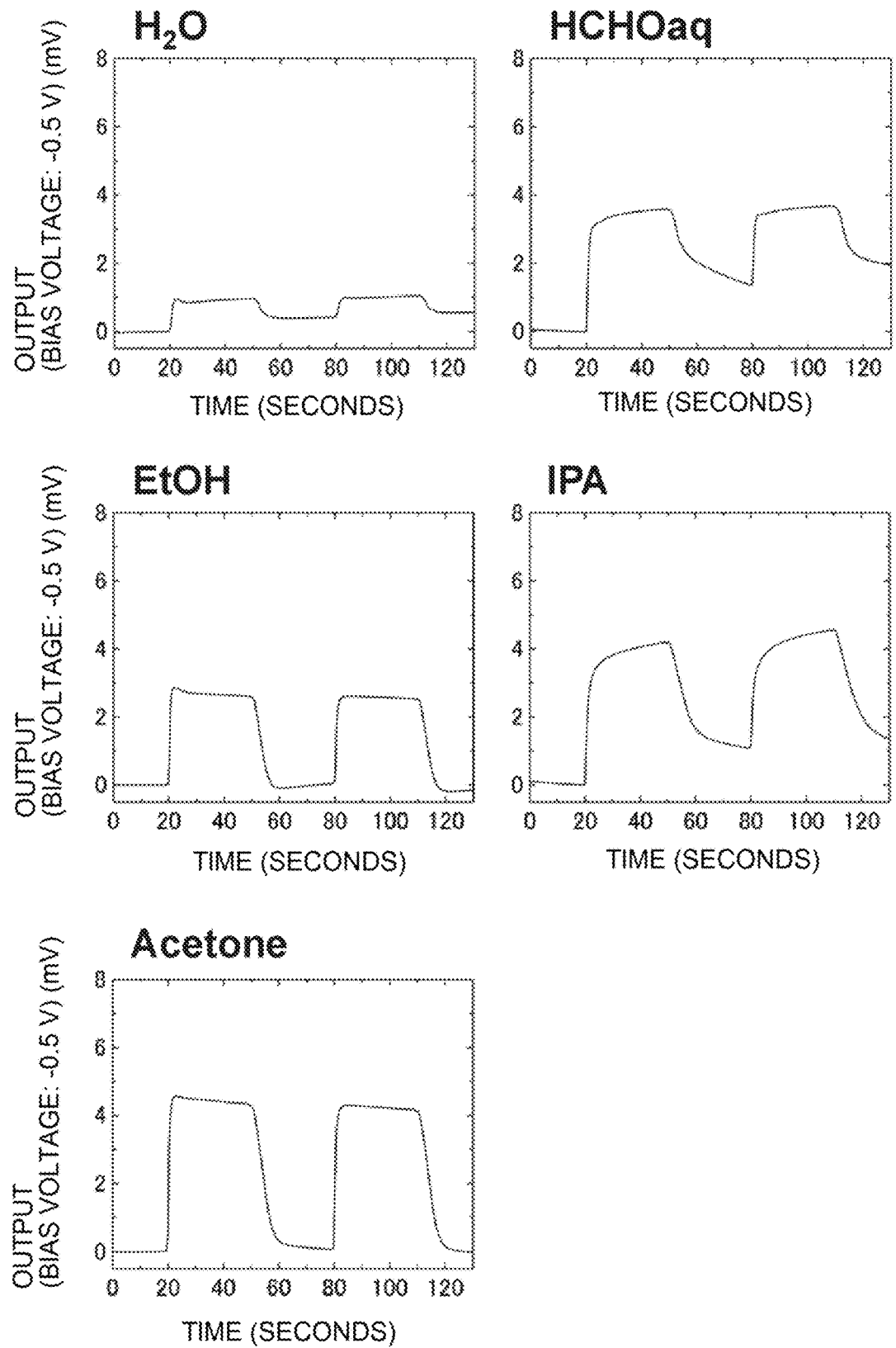
FIG. 16A is a drawing illustrating a part of the result of measuring nine kinds of compound by using MSS coated with ZIF-7 nanoparticles of which SEM image is shown in FIG. 15.
Figure 16B:
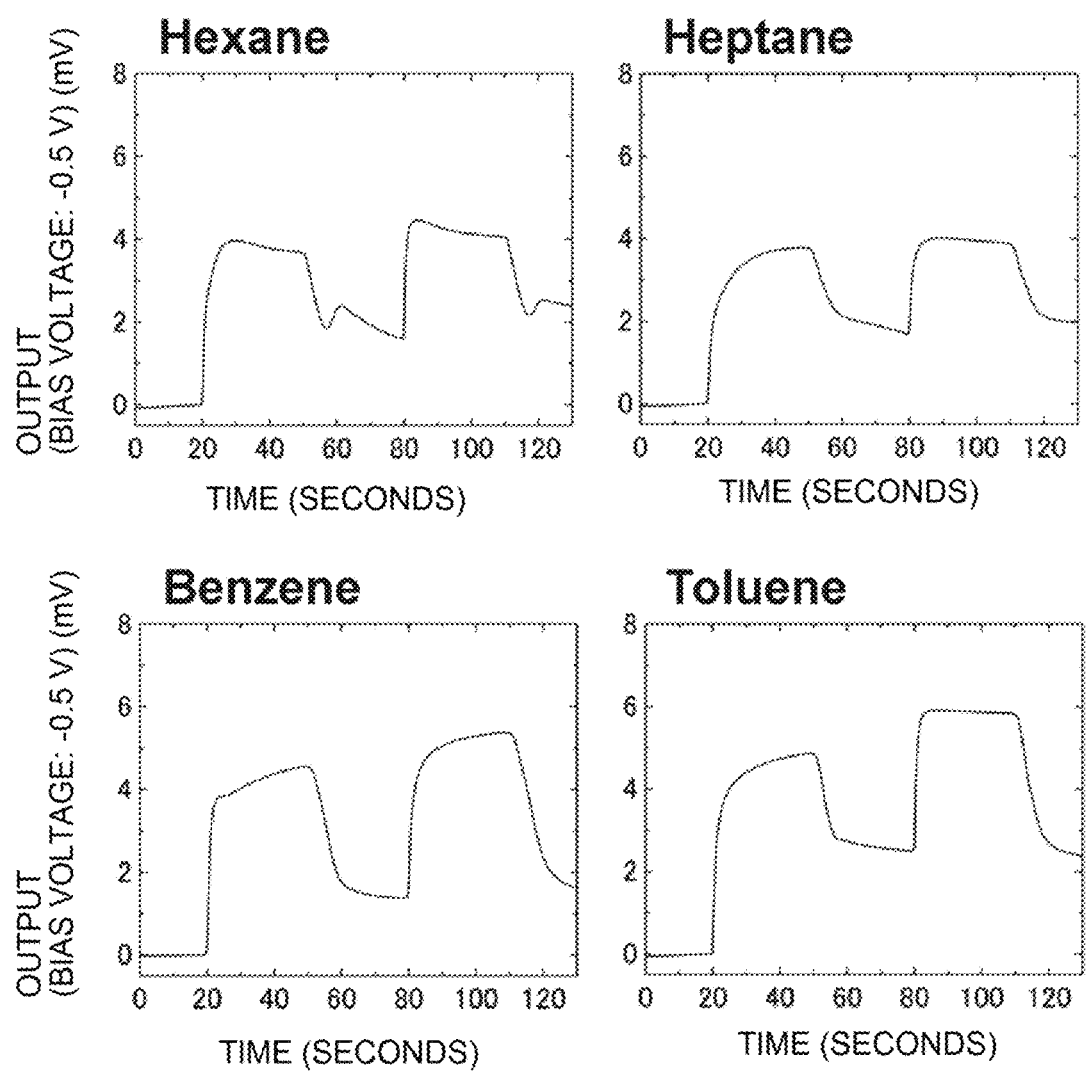
FIG. 16B is a drawing illustrating the remaining result of measuring nine kinds of compound by using MSS coated with ZIF-7 nanoparticles of which SEM image is shown in FIG. 15.
Figure 17A:
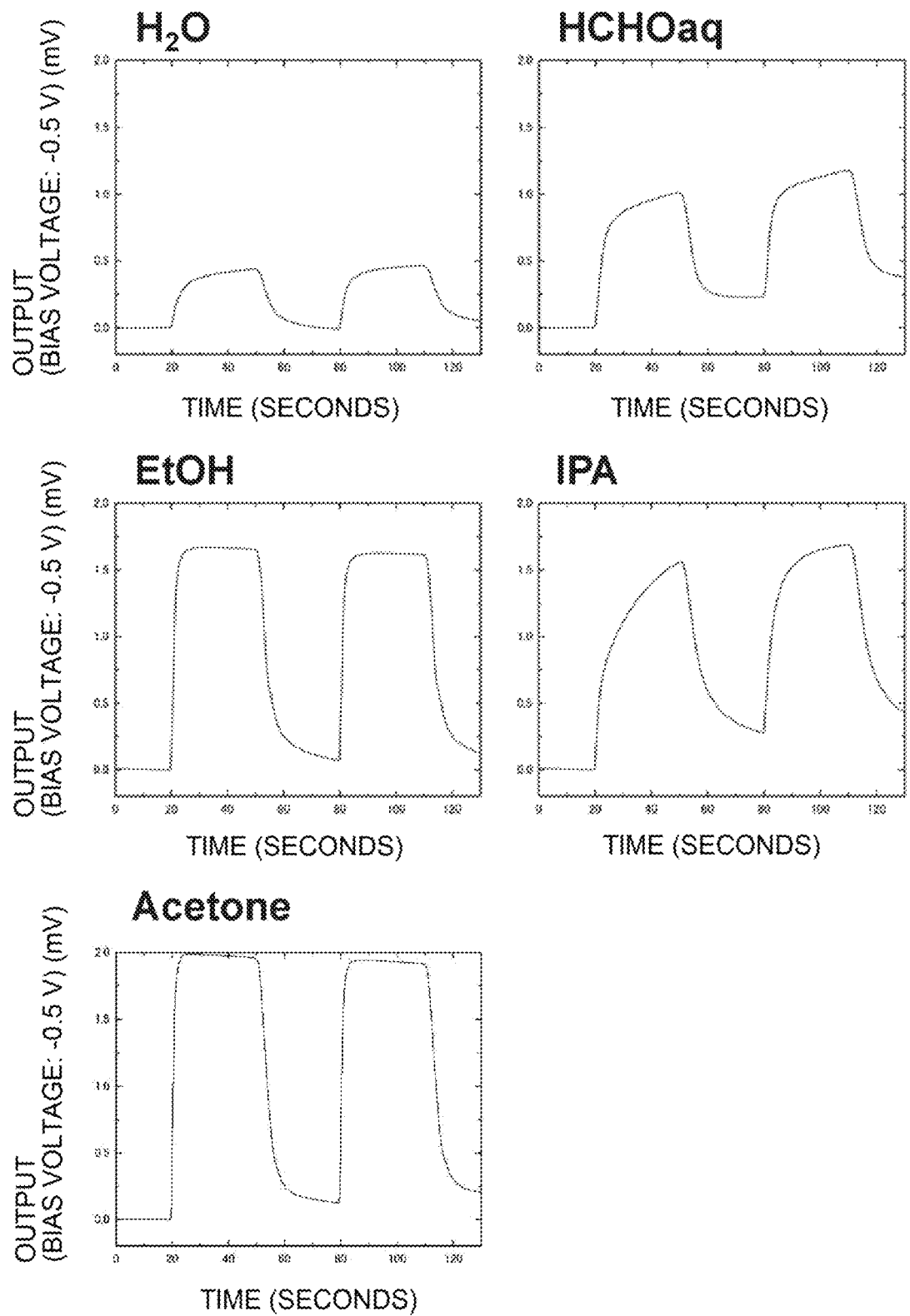
FIG. 17A is a drawing illustrating a part of the result of measuring nine kinds of compound by using MSS coated with ZIF-8 nanoparticles of which SEM image is shown in FIG. 15.
Figure 17B:
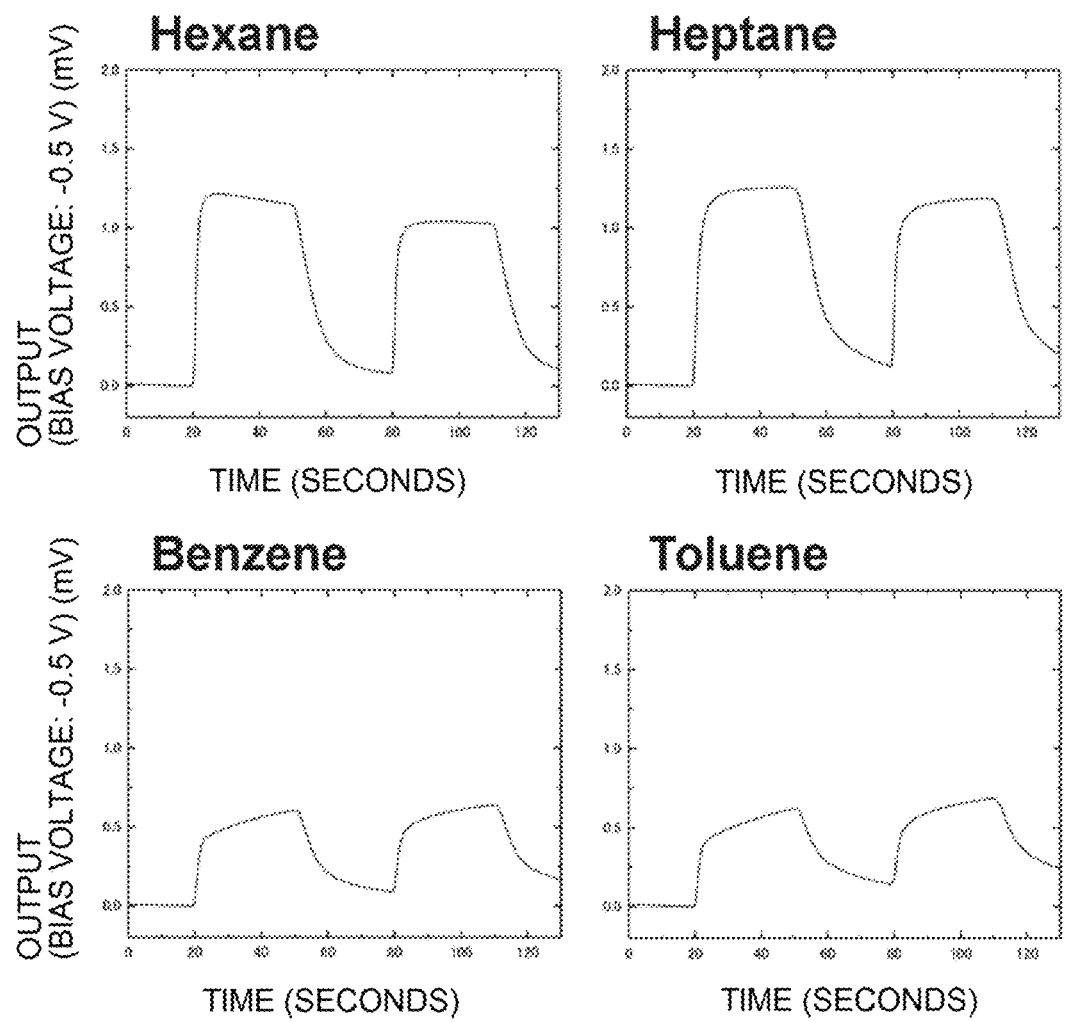
FIG. 17B is a drawing illustrating the remaining result of measuring nine kinds of compound by using MSS coated with ZIF-8 nanoparticles of which SEM image is shown in FIG. 15.
Figure 18A:
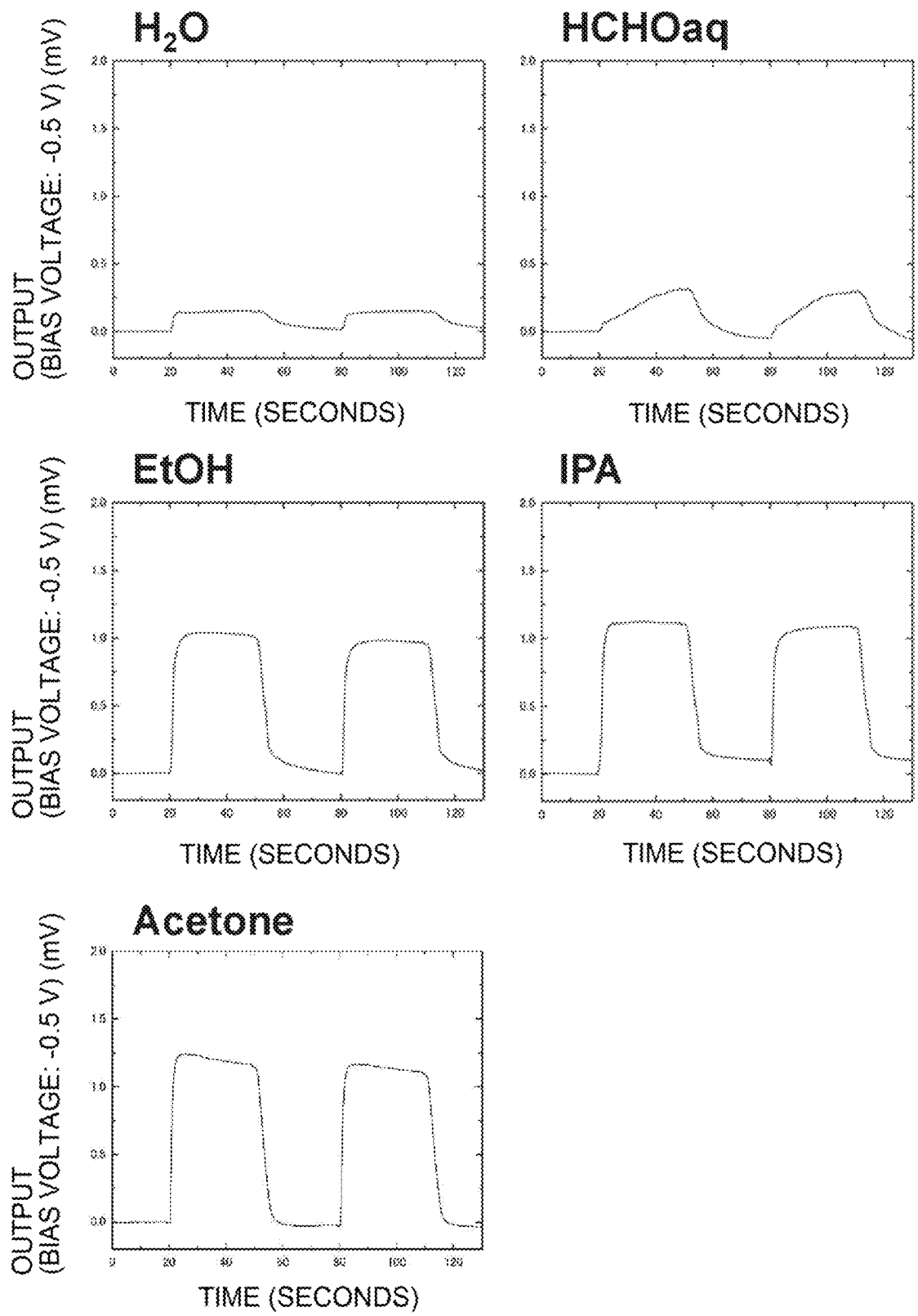
FIG. 18A is a drawing illustrating a part of the result of measuring nine kinds of compound by using MSS coated with ZIF-71 nanoparticles of which SEM image is shown in FIG. 15.
Figure 18B:
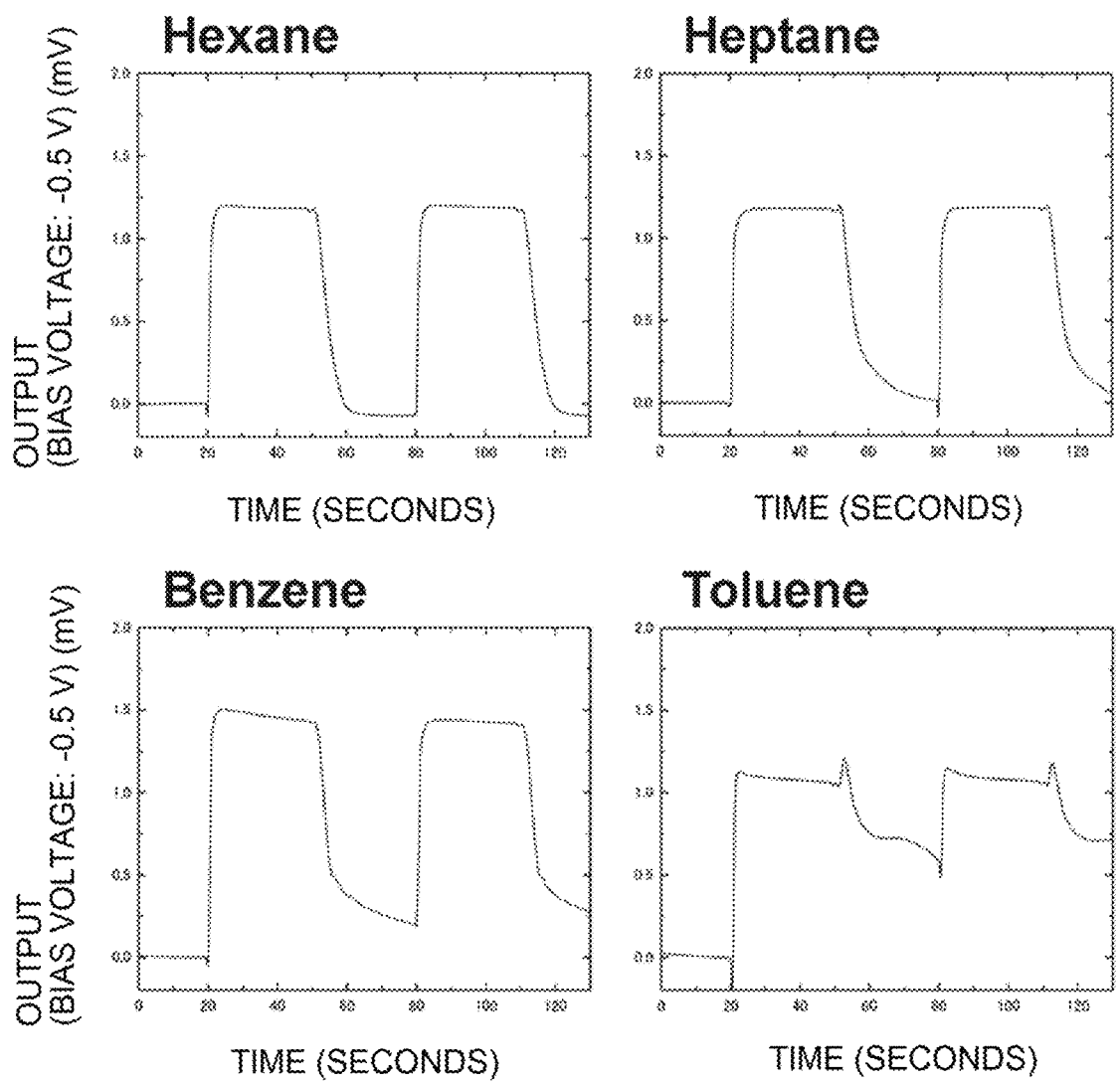
FIG. 18B is a drawing illustrating the remaining result of measuring nine kinds of compound by using MSS coated with ZIF-71 nanoparticles of which SEM image is shown in FIG. 15.

<Example 6> MSS Having Receptor Layer Coated with Metal Organic Framework (MOF) Nanoparticles Various materials other than those described above can be used for a receptor layer. As an example of such other material, MSSs having receptor layers formed with MOF nanoparticles were prepared, and the detection properties for various compounds were measured. As for the MOFs, ZIF-7, ZIF-8, and ZIF-71 of which crystal structure diagrams and SEM images of nanoparticles are shown in FIG. 15 were used. Although the method for producing those MOF nanoparticles are well known as explained in Non Patent Literature 5 to 7, brief explanations are given hereunder.

[Synthesis of ZIF-7 Nanoparticles]

Based on Non Patent Literature 5, nanoparticles were synthesized as follows. First, zinc nitrate hexahydrate (302 mg, 1.02 mmol) was dissolved in N,N-dimethyl formamide (10 mL), and the resulting solution was rapidly added to a solution of benzimidazole (769 mg, 6.4 mmol) in N,N-dimethyl formamide (10 mL) under stirring at room temperature. After stirring continuously for 12 hours, the resulting milky white suspension was subjected to centrifuge at 15000×g for 30 minutes. The supernatant was carefully decanted and replaced with methanol. The mixture was then subjected to an ultrasonic wave treatment for 1 minute to redisperse the particulate material. The centrifuge/washing treatment was repeated an additional 3 times. Half of the suspension obtained accordingly was saved for separate use, and the remaining half was dried (2 to 3 hours in air at 60° C., and subsequently overnight at 180° C. under continuous vacuum) to obtain 104 mg of yellowish white solid (yield of 71% based on Zn).

[Synthesis of ZIF-8 Nanoparticles]

Based on Non Patent Literature 6, nanoparticles were synthesized as follows. First, zinc nitrate hexahydrate (297 mg, 1 mmol) was dissolved in methanol (20 mL), and the resulting solution was rapidly added to a solution of 2-methylimidazole (649 mg, 7.9 mmol) in methanol (20 mL) under stirring. After stirring continuously for 6 hours and 30 minutes, the resulting milky white suspension was subjected to centrifuge at 15000×g for 1 hour. The supernatant was carefully decanted and replaced with fresh methanol. The mixture was then subjected to an ultrasonic wave treatment for 5 minutes to redisperse the particulate material. The centrifuge/washing treatment was repeated an additional 2 times. Half of the suspension obtained accordingly was saved for separate use, and the remaining half was dried (2 to 3 hours in air at 90° C., and subsequently overnight at 180° C. under continuous vacuum) to obtain 38 mg of pale yellow solid (yield of 35% based on Zn).

[Synthesis of ZIF-71 Nanoparticles]

Based on Non Patent Literature 6, nanoparticles were synthesized as follows. First, anhydrous zinc acetate (220 mg, 1 mmol) was dissolved in N,N-dimethyl formamide (10 mL), and the resulting solution was rapidly added to a solution of 4,5-dichloroimidazole (960 mg, 6 mmol) in N,N-dimethyl formamide (10 mL) under stirring at room temperature. After stirring continuously for 4 hours, the resulting milky white suspension was subjected to centrifuge at 15000×g for 30 minutes. The supernatant was carefully decanted and replaced with methanol. The mixture was then subjected to an ultrasonic wave treatment for 1 minute to redisperse the particulate material. The centrifuge/washing treatment was repeated an additional 3 times. Half of the suspension obtained accordingly was saved for separate use, and the remaining half was dried (in air at 60° C., and subsequently overnight at 180° C. under continuous vacuum) to obtain 104 mg of a grayish white solid (yield of 71% based on Zn). Half of the suspension obtained accordingly was saved for separate use, and the remaining half was dried (2 to 3 hours in air at 60° C., and subsequently overnight at 180° C. while continuing the vacuuming process under vacuum) to obtain 75 mg of brown powder (yield of 46% based on Zn).

An MSS was coated with each of those three kinds of MOF nanoparticles, and after applying intermittently at pre-determined periods nine kinds of compound, specifically, water vapor ($H_2O$), formalin (HCHOaq), ethanol (EtOH), isopropanol (IPA), acetone (Acetone), hexane (Hexane), heptane (Heptane), benzene (Benzene), or toluene (Toluene), a change in detection output from the MSS over time was measured in the same manner as Example 2. Because the methods for coating MSS with ZIF-7, ZIF-8, or ZIF-71 were not the same each other, the thicknesses of the receptor layers are different for different types of MOF. Thus, the absolute values of detection properties cannot be compared among different MOFs. However, because the measurement conditions other than receptor layer thickness were fixed as much as possible, the detection properties can be compared as far as the same MOF is used. Furthermore, trends in the detection properties in the case of changing the sample material can be also compared between different MOFs. The detection output obtained by having ZIF-7, ZIF-8, and ZIF-71 as a receptor layer is shown in FIGS. 16A and 16B, FIGS. 17A and 17B, and FIGS. 18A and 18B, respectively.

Figure 19:
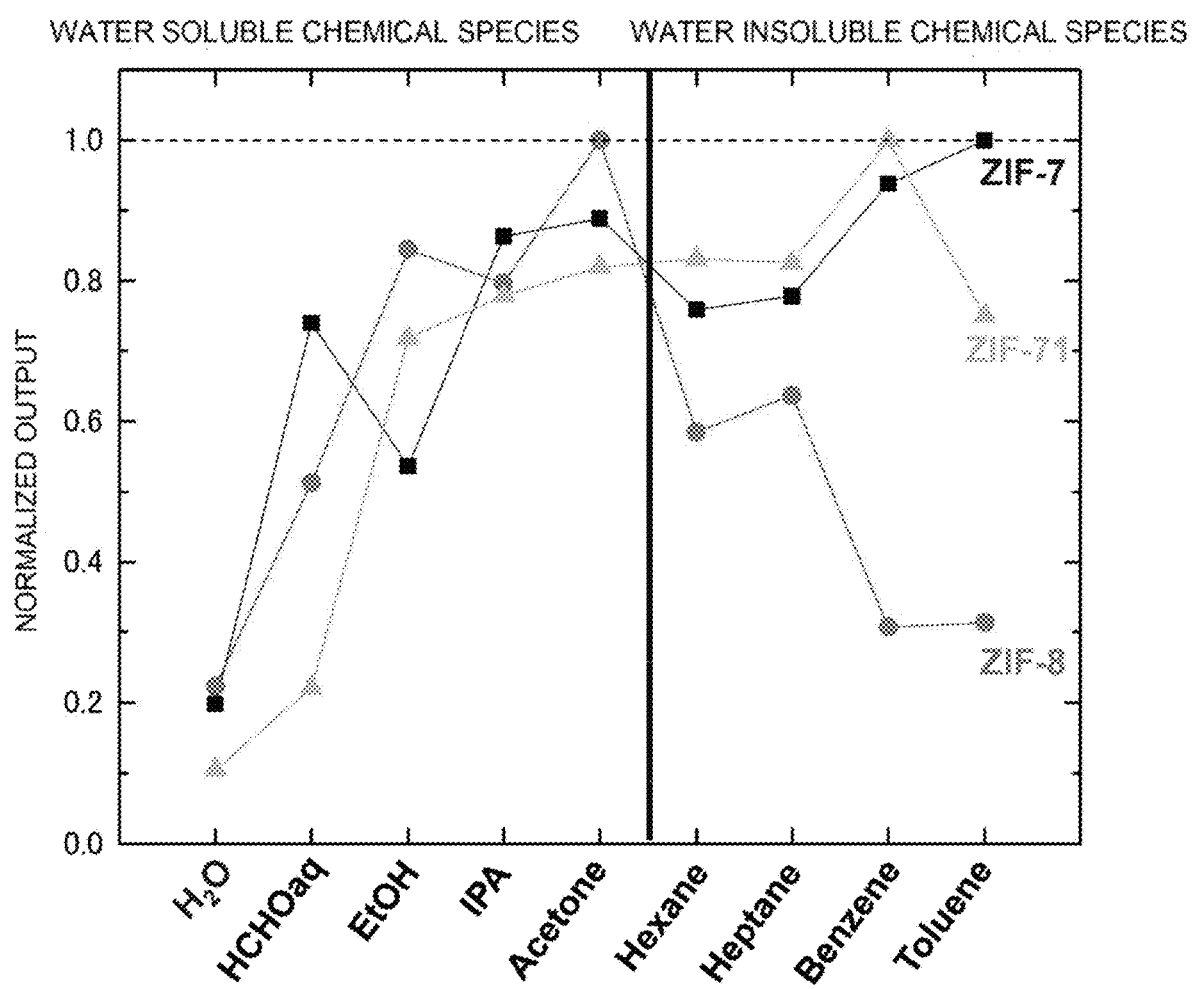
FIG. 19 is a drawing illustrating the trend of affinity of each nanoparticle for a polar or nonpolar compound, in which the trend is derived from the result of measurement using MSS coated with three kinds of MOF nanoparticles of which SEM image is shown in FIG. 15.

Furthermore, a graph in which the peak values of the time changing detection output obtained as above (specifically, detection output obtained 30 seconds after starting injection of sample gas) is plotted is shown in FIG. 19. The peak values in the graph are normalized against the maximum peak value for each MOF nanoparticle. From the graph, the approximate affinity of each MOF for each polar or nonpolar compound can be estimated.

Figure 20:
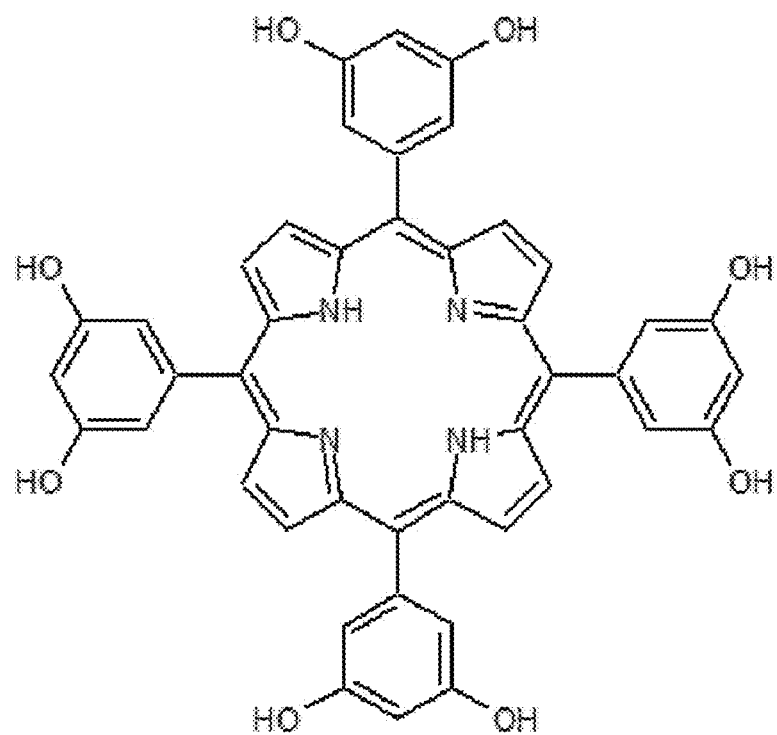
FIG. 20 is a drawing illustrating the structural chemical formula of T(3,5-DHP)P(5,10,15,20-tetrakis(3',5'-dihydroxyphenyl)porphyrin, Por-OH) as an example of a porphyrin which is combined with graphene oxide (GO).
Figure 24:
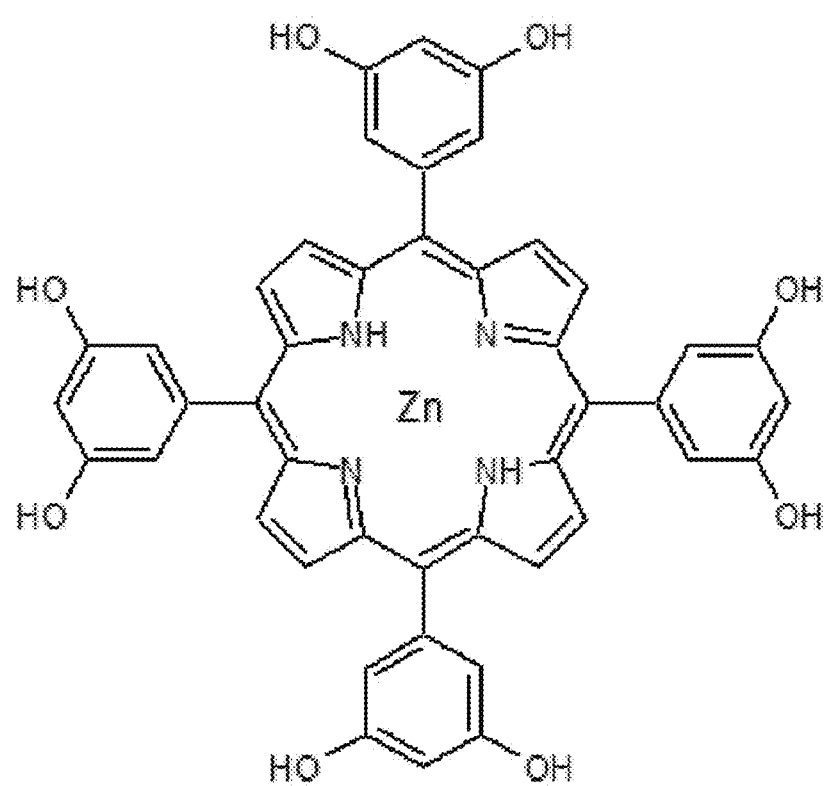
FIG. 24 is a drawing illustrating the structural chemical formula of Zn-T(3,5-DHP)P(5,10,15,20-tetrakis(3',5'-dihydroxyphenyl)porphinatozi nc(II), Zn-Por-OH) as another example of a porphyrin to be combined with graphene oxide (GO).

<Example 7> MSS Having Receptor Layer in which Graphene Oxide (GO) and Porphyrin are Combined After forming a film of receptor layer, which has been formed by combining graphene oxide (GO) with porphyrin, on an MSS, detection output for various compounds was determined. As for the porphyrin, T(3,5-DHP)P(5,10,15,20-tetrakis(3',5'-dihydroxyphenyl)porphyrin, Por-OH) of which chemical formula is shown in FIG. 20 and Zn-T(3,5-DHP)P(3',5'-dihydroxyphenyl)porphinato zinc (II), Zn-Por-OH) of which chemical formula is shown in FIG. 24 were used. As described in Non Patent Literature 8, GO is known to easily possess a porous property. The receptor layer of this Example has a structure in which the porphyrin (Por-OH, Zn-Por-OH) is applied in a porous GO network. In the SEM image described below, although an observation is made for the spin coating of a small amount on a Si substrate to have clear view of each sheet, those applied on the sensor film are considered to form a porous network as described in Non Patent Literature 8.

[Por-OH+GO]

An aqueous solution of GO (about 100 mg/L) and a Por-OH methanol solution (1 mM) were prepared, and by modifying the mixing ratio of them, the following three kinds of solution in which Por-OH and GO are mixed were prepared.

(1) Aqueous solution of GO 500 µL+Por-OH methanol solution 10
(2) Aqueous solution of GO 500 µL+Por-OH methanol solution 100
(3) Aqueous solution of GO 500 µL+Por-OH methanol solution 1000

Figure 21:
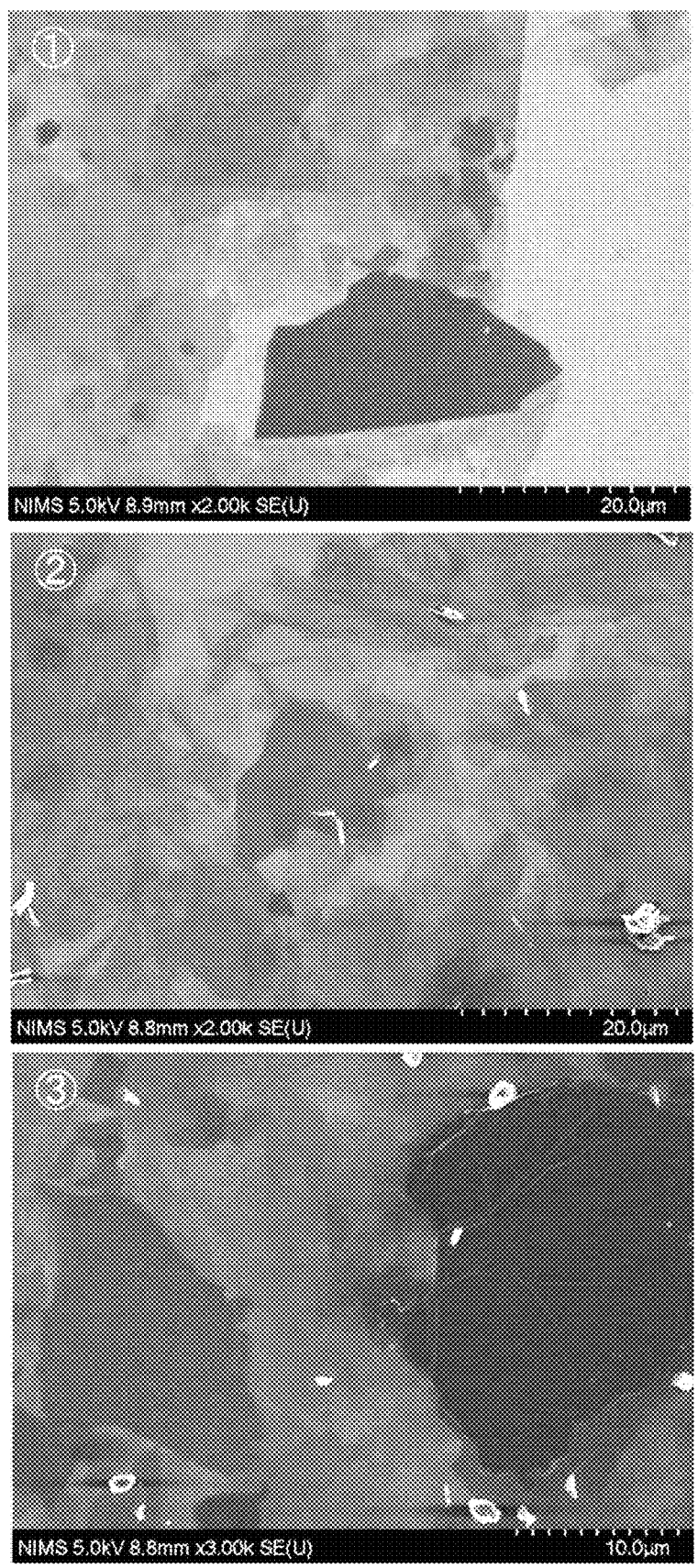
FIG. 21 is a SEM image showing the state in which a combination of GO and Por-OH is applied on a substrate.

The SEM image obtained after coating a Si substrate with the mixed solutions (1) to (3) by spin coating followed by drying is shown with the circled numbers 1 to 3 in FIG. 21.

By forming a film of each of the mixed solutions (1) to (3) on an MSS by inkjet method, MSS Ch1 to Ch3 having a receptor layer were prepared.

Ch1: spraying 250 shots of the mixed solution (1)
Ch2: spraying 250 shots of the mixed solution (2)
Ch3: spraying 750 shots of the mixed solution (3)

Figure 22:
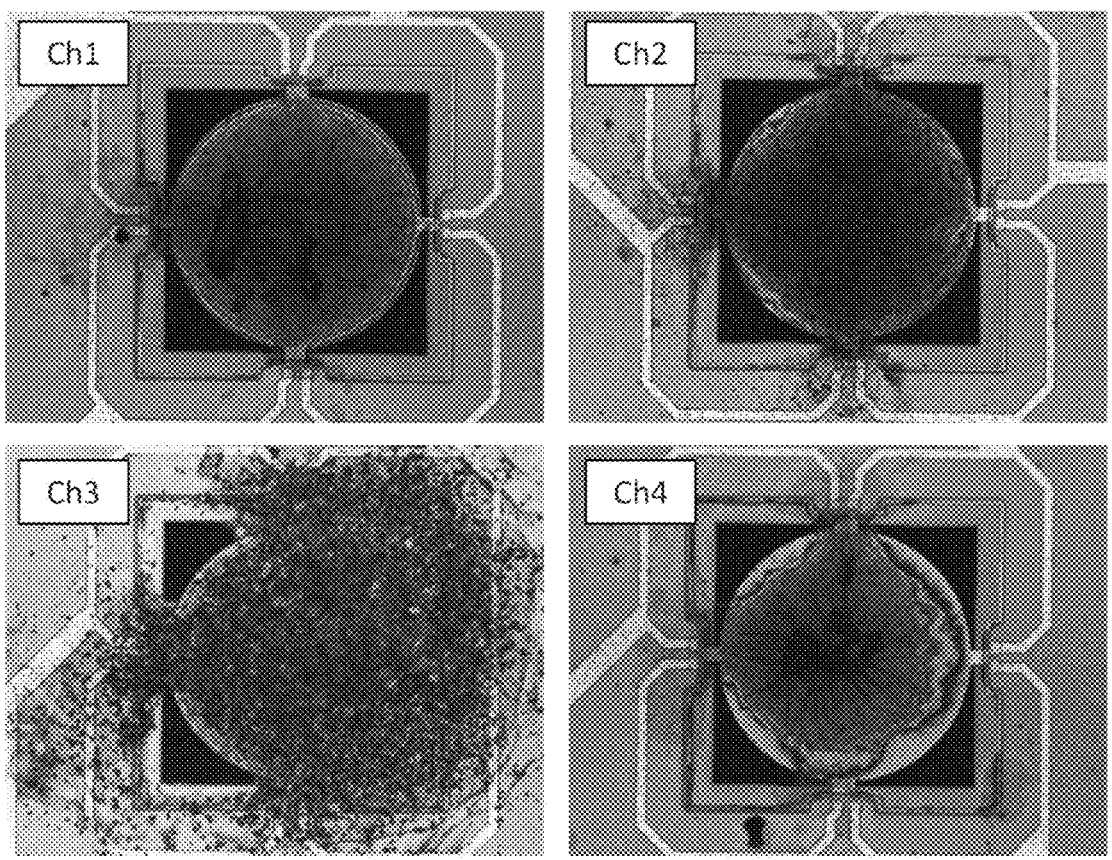
FIG. 22 is an optical microscope image of (a) surface and (b) back surface of MSS having a membrane which is formed of a combination of GO and Por-OH (Ch1 to Ch3) and an aqueous solution of GO (Ch4) by using an inkjet method.
Figure 22:
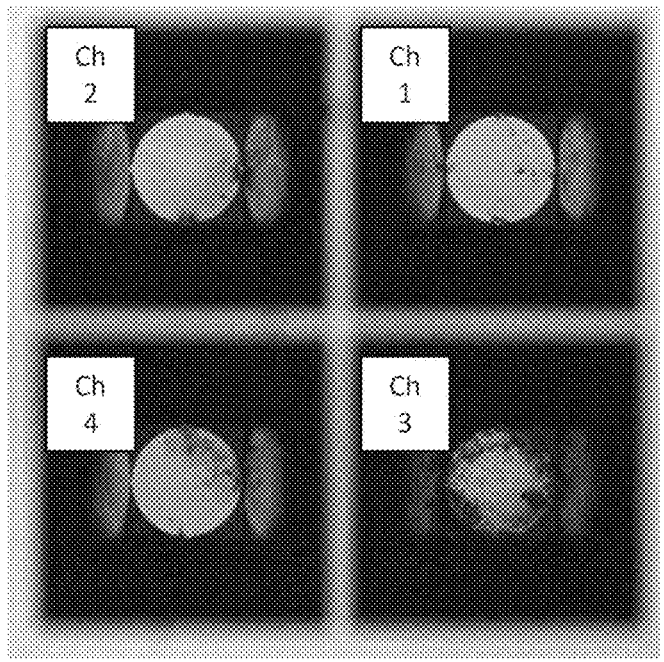

Furthermore, by spraying 250 shots of an aqueous solution of GO by inkjet method on an MSS, MSS Ch4 having a receptor layer was prepared as a comparative subject. The photographs of the surface (i.e., inkjet-sprayed side) and back surface (i.e., opposite side to the inkjet-sprayed side) of MSS Ch1 to Ch4 prepared above, in which the photographs are taken through a microscope, are shown in (a) and (b) of FIG. 22, respectively.

Figure 23:
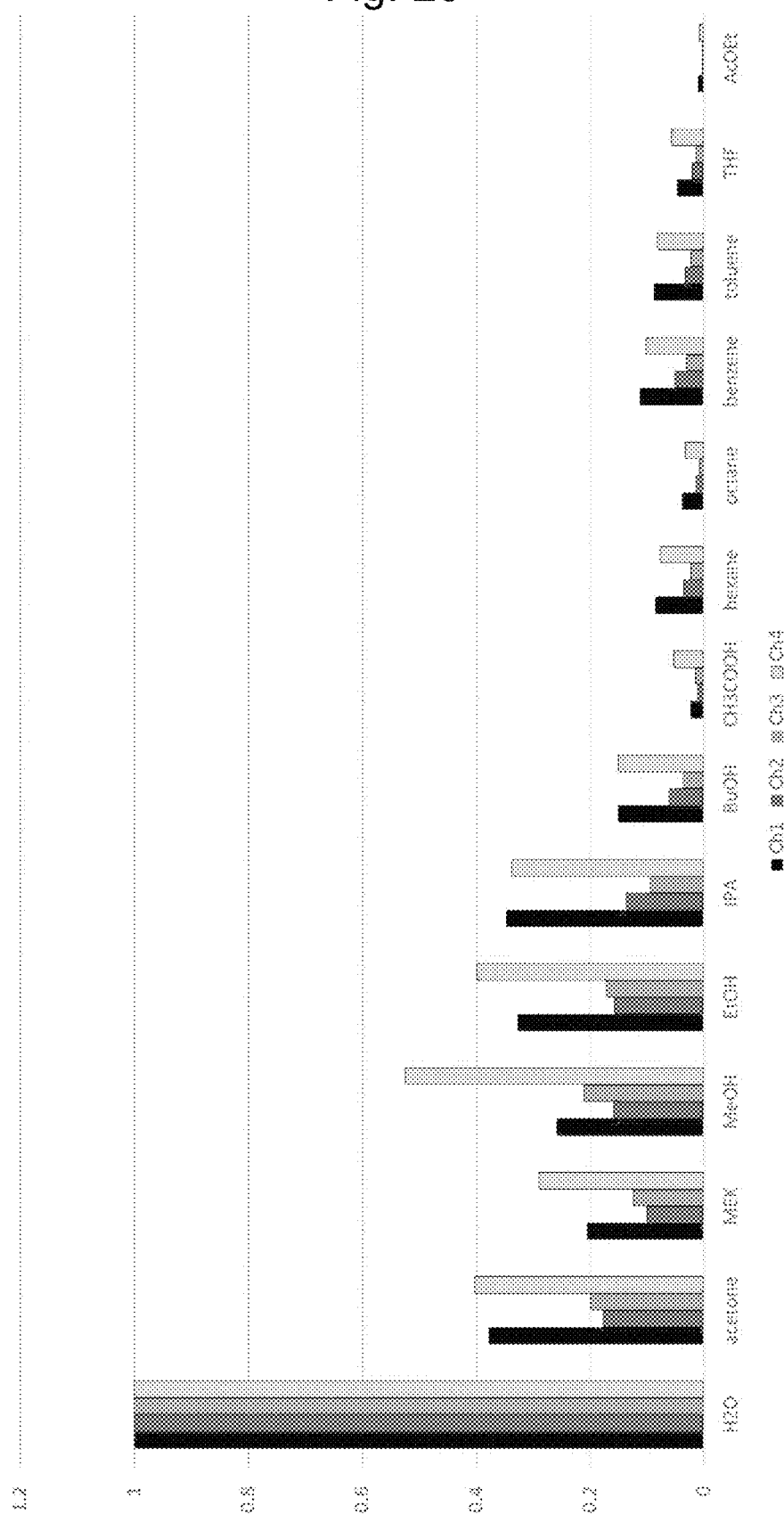
FIG. 23 is a drawing illustrating the result of measuring 14 kinds of compound by using MSS coated with four kinds of receptor shown in FIG. 22 (Ch1 to Ch4).

By using those four kinds of MSS prepared above, measurements for 14 kinds of compound, i.e., water ($H_2O$), acetone (acetone), methyl ethyl ketone (MEK), methanol (MeOH), ethanol (EtOH), isopropanol (IPA), butanol (BuOH), acetic acid ($CH_3COOH$), hexane (hexane), octane (octane), benzene (benzene), toluene (toluene), tetrahydrofuran (THF), and ethyl acetate (AcOEt), were carried out and the resultant graph is shown in FIG. 23. The measurement was performed under the same conditions as the previous example, i.e., Example 6. For MSS Ch1 to Ch4 in the graph, each measurement value was normalized against the measurement value for water. Regarding this graph, when the detection output of Ch1 to Ch3 which have a receptor layer in which GO is combined with Por-OH is compared to the detection output of Ch4 which has a receptor layer consisting of GO only, it was found that the selectivity for water is higher if GO is combined with Por-OH compared to a case of having GO only (i.e., in the graph, detection output for the compounds other than water is smaller).

[Zn-Por-OH+GO]

An aqueous solution of GO (about 100 mg/L) and Zn-Por-OH methanol solution (1 mM) were prepared, and by modifying the mixing ratio of them, the following three kinds of solution in which Por-OH and GO are mixed were prepared.

Figure 25:
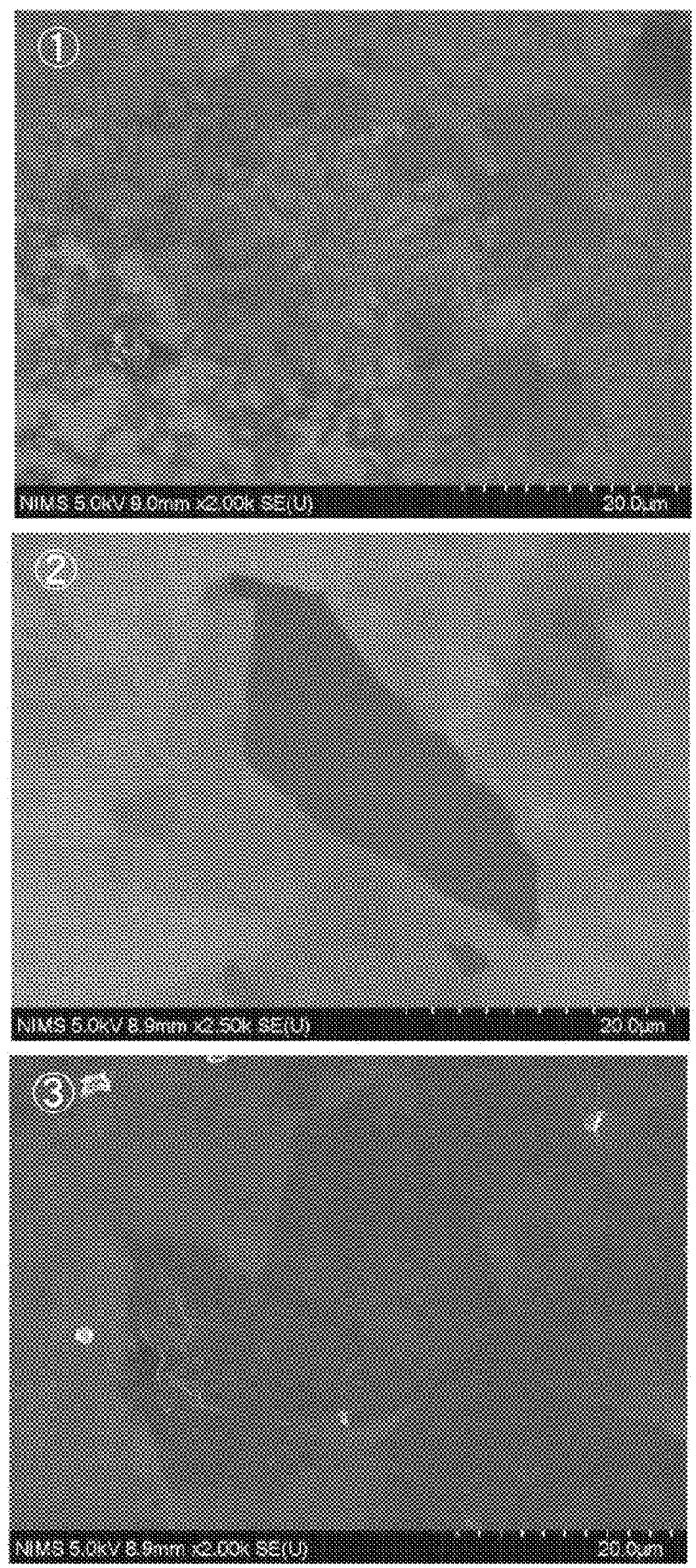
FIG. 25 is a SEM image showing the state in which a combination of GO and Zn-Por-OH is applied on a substrate.

(1') Aqueous solution of GO 500 µL+Por-OH methanol solution 10 µL
(2') Aqueous solution of GO 500 µL+Por-OH methanol solution 100 µL
(3') Aqueous solution of GO 500 µL+Por-OH methanol solution 1000 µL The SEM image obtained after coating a Si substrate with the mixed solutions (1') to (3') by spin coating followed by drying is shown with the circled numbers 1 to 3 in FIG. 25.

By forming a film of each of the mixed solutions (1') to (3') on an MSS by inkjet method, MSS Ch1 to Ch3 having a receptor layer were prepared.

Ch1: spraying 250 shots of the mixed solution (1')
Ch2: spraying 250 shots of the mixed solution (2')
Ch3: spraying 750 shots of the mixed solution (3')

Figure 26:
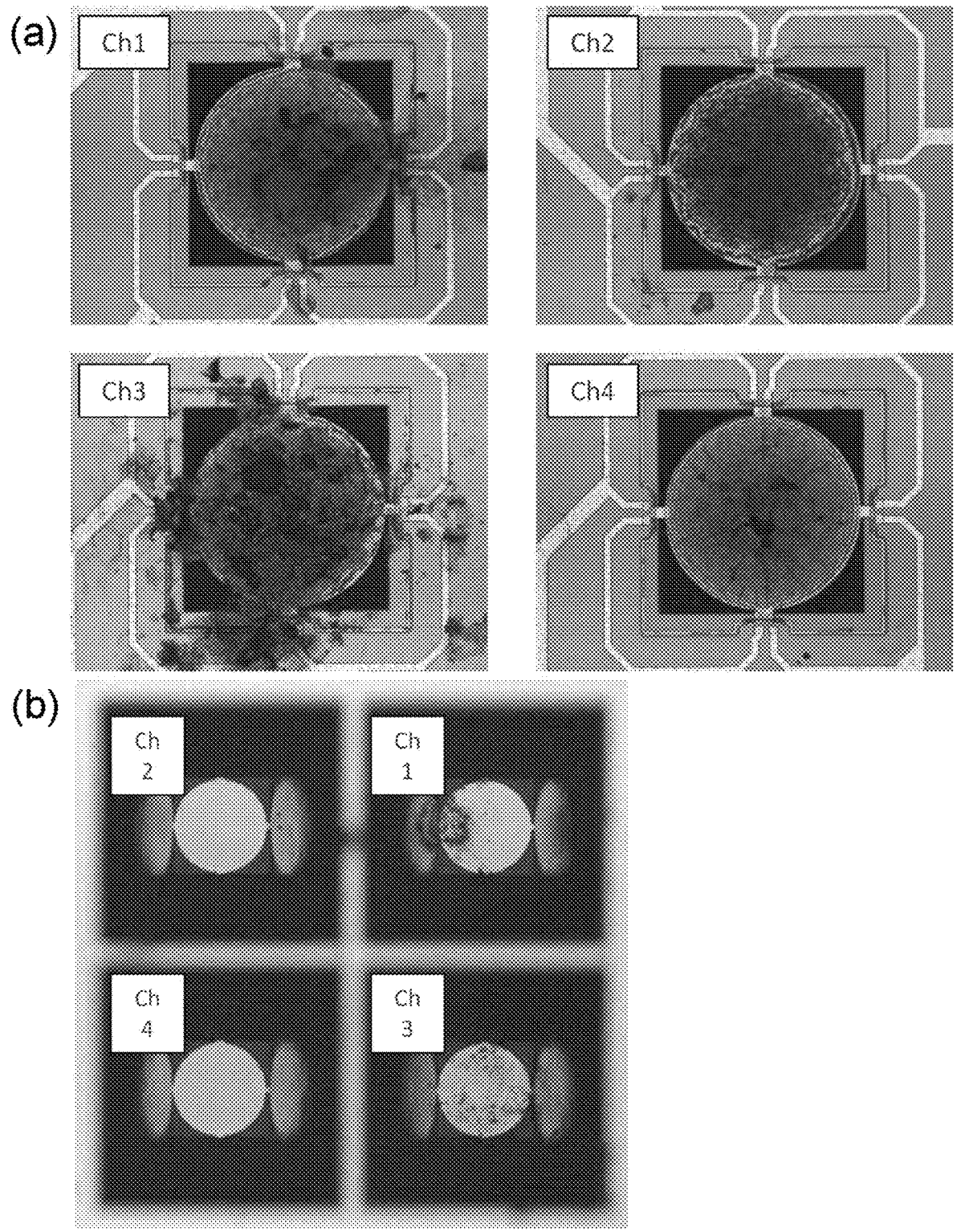
FIG. 26 is an optical microscope image of (a) surface and (b) back surface of MSS having a membrane which is formed of a combination of GO and Zn-Por-OH (Ch1 to Ch3) and an aqueous solution of GO (Ch4) by using an inkjet method.

Furthermore, by spraying 250 shots of an aqueous solution of GO by inkjet method on an MSS, MSS Ch4 having a receptor layer was prepared as a comparative subject. The photographs of the surface (i.e., inkjet-sprayed side) and back surface (i.e., opposite side to the inkjet-sprayed side) of MSS Ch1 to Ch4 prepared above, in which the photographs are taken through a microscope, are shown in (a) and (b) of FIG. 26, respectively.

Figure 27:
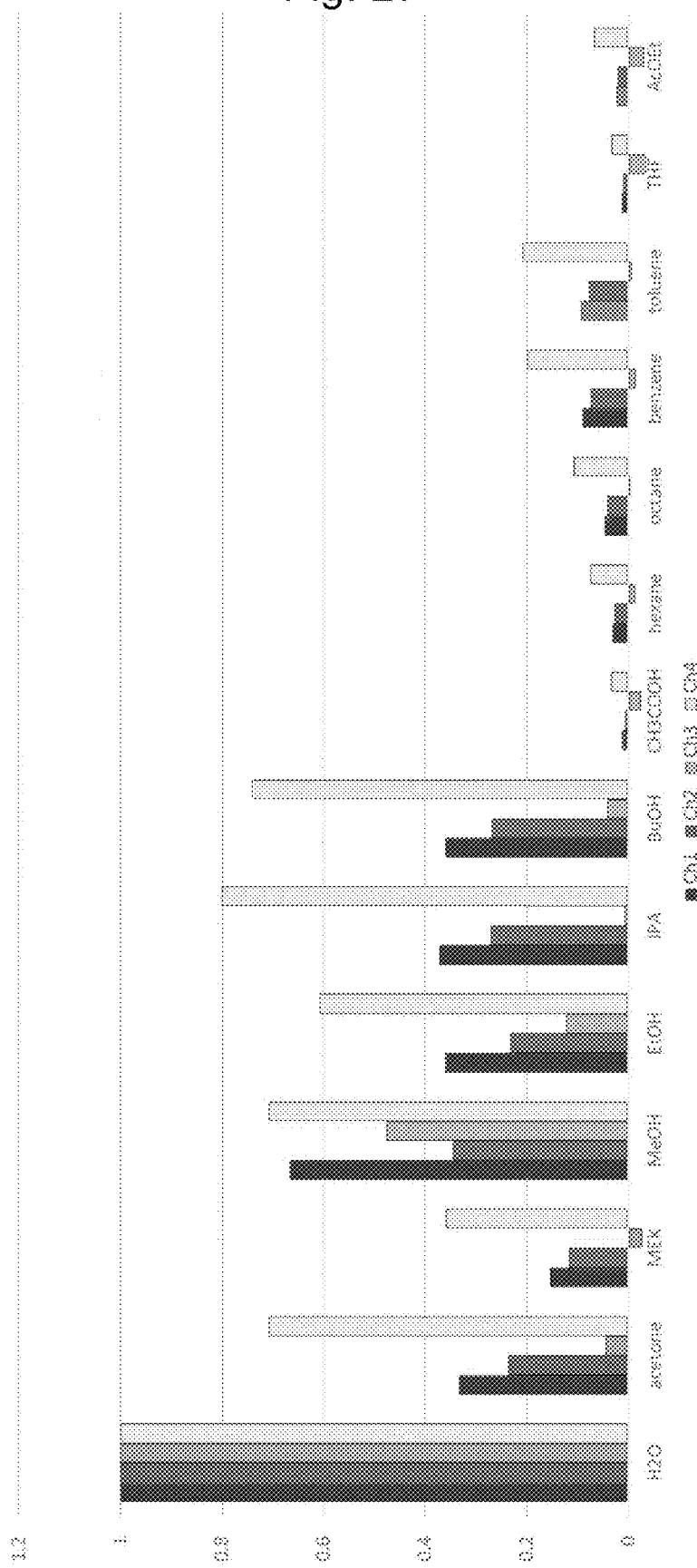
FIG. 27 is a drawing illustrating the result of measuring 14 kinds of compound by using MSS coated with four kinds of receptor shown in FIG. 26 (Ch1 to Ch4).

By using those four kinds of MSS prepared above, measurements for 14 kinds of compound, i.e., water ($H_2O$), acetone (acetone), methyl ethyl ketone (MEK), methanol (MeOH), ethanol (EtOH), isopropanol (IPA), butanol (BuOH), acetic acid ($CH_3COOH$), hexane (hexane), octane (octane), benzene (benzene), toluene (toluene), tetrahydrofuran (THF), and ethyl acetate (AcOEt), were carried out in the same manner as Por-OH+GO and the resultant graph is shown in FIG. 27. This measurement was performed under the same conditions as the previous example, i.e., Example 6, too. For MSS Ch1 to Ch4 in the graph, each measurement value was normalized against the measurement value for water. Regarding this graph, when the detection output of Ch1 to Ch3 which have a receptor layer in which GO is combined with Zn-Por-OH is compared to the detection output of Ch4 which has a receptor layer consisting of GO only, it was found that the selectivity for water is also higher if GO is combined with Zn-Por-OH compared to a case of having GO only (i.e., in the graph, detection output for the compounds other than water is smaller).

LIST OF CITATIONS

Patent Literature

Patent Literature 1: WO 2011/148774 A1

Non Patent Literature

Non Patent Literature 1: G. Yoshikawa, "Mechanical Analysis and Optimization of a Microcantilever Sensor Coated with a Solid Receptor Film," Appl. Phys. Lett. 98, 173502-1-173502-3 (2011).

Non Patent Literature 2: G. Yoshikawa, C. J. Y. Lee and K. Shiba, "Effects of Coating Materials on Two Dimensional Stress-Induced Deflection of Nanomechanical Sensors," J. Nanosci. Nanotechnol. 14, 2908-2912 (2013).

Non Patent Literature 3: W. Heni, L. Vonna and H. Haidara, "Experimental Characterization of the Nanoparticle Size Effect on the Mechanical Stability of Nanoparticle-Based Coatings," Nano Lett. 15, 442-449 (2015).

Non Patent Literature 4: K. Shiba and M. Ogawa, "Microfluidic syntheses of well-defined sub-micron nanoporous titania spherical particles," Chem. Commun. 6851-6853 (2009).

Non Patent Literature 5: Yan-Shuo Li, Fang-Yi Liang, Helge Bux, Armin Feldhoff, Wei-Shen Yang, and Juergen Caro, "Molecular Sieve Membrane: Supported Metal. Organic Framework with High Hydrogen Selectivity," Angew. Chem. Int. Ed., 49, 548-551 (2010).

Non Patent Literature 6: Janosch Cravillon, Simon Muenzer, Sven-Jare Lohmeier, Armin Feldhoff, Klaus Huber, and Michael Wiebcke, "Rapid Room-Temperature Synthesis and Characterization of Nanocrystals of a Prototypical Zeolitic Imidazolate Framework," Chem. Mater. 21, 1410-1412 (2009).

Non Patent Literature 7: Min Tu, Christian Wiktor, Christoph Roesler and Roland A. Fischer, "Rapid room temperature syntheses of zeolitic-imidazolate framework (ZIF) nanocrystals," Chem. Commun. 50 13258 (2014).

Non Patent Literature 8: Lili Jiang and Zhuangjun Fan, "Design of advanced porous graphene materials: from graphene nanomesh to 3D architectures," Nanoscale, 6, 1922-1945 (2014).

The invention claimed is:

1. A surface stress sensor comprising:
a sensor body for detecting a surface stress; and
a particulate material coated over the sensor body;
wherein a sample molecule is detected based on a change in the surface stress caused by adsorption of the sample molecule by the particulate material.

2. The surface stress sensor according to claim 1, wherein the particulate material consists of an inorganic material.

3. The surface stress sensor according to claim 1, wherein the particulate material is selected from a group consisting of an inorganic material, an organic material, an inorganic-organic hybrid material, a metal organic framework, a material with a self-assembled surfactant micelle incorporated in its structure, and a biomaterial.

4. The surface stress sensor according to claim 3, wherein
the inorganic material is one or more materials selected from a group consisting of oxide, nitride, sulfide, metal, and gold, or an inorganic matter containing a composite of a plurality of materials selected from the group at any ratio,
the organic material is an organic matter having, in the structure, a polymerizable functional group as a main chain and a substituent group in a side chain,
the inorganic-organic hybrid material is selected from a group consisting of an inorganic-organic hybrid which is a composite of an inorganic material and an organic material at any ratio,
the metal organic framework is selected from a group consisting of HKUST-1, IRMOF, MOF, ZIF, U10, and MIL,
the material with a self-assembled surfactant micelle incorporated in the structure is selected from a group consisting of a material with a cationic surfactant incorporated in silica structure and a material with a block copolymer incorporated in a metal skeleton, and
the biomaterial is a material selected from a peptide, an enzyme, a sugar, a lipid, and a protein, or a composite of a material selected from a peptide, an enzyme, a sugar, a lipid, and a protein and the inorganic material.

5. The surface stress sensor according to claim 4, wherein the composite in at least one of the inorganic material and the inorganic-organic hybrid material is of a configuration selected from a group consisting of a configuration of a heterogeneous binding in a manner of a Janus particle, a core-shell configuration, and a configuration in which a plurality of one type of particles are dispersed within the other type of particle.

6. The surface stress sensor according to claim 4, wherein the organic material is selected from a group consisting of polystyrene, polymethyl methacrylate, polydivinyl benzene, polyisopropyl acrylamide, porphyrin, a compound with a substituent group introduced to a porphyrin ring, and a porphyrin-metal complex compound having a transition metal.

7. The surface stress sensor according to claim 1, wherein the particulate material is a nanoparticle.

8. The surface stress sensor according to claim 1, wherein the coating formed by the particulate material contains a void, such that the coating is porous.

9. The surface stress sensor according to claim 1, wherein the particulate material has a particle size of 1 mm or less.

10. The surface stress sensor according to claim 1, wherein the particulate material has a porous structure.

11. A surface stress sensor comprising:
a sensor body for detecting a surface stress; and
a porous or particulate material coated over the sensor body;
wherein a sample molecule is detected based on a change in the surface stress caused by adsorption of the sample molecule by the porous or particulate material, and
wherein the surface of the porous or particulate material is modified with one or a plurality of surface modifying groups.

12. The surface stress sensor according to claim 11, wherein at least one of the surface modifying groups adsorbs the sample molecule.

13. The surface stress sensor according to claim 11, wherein,
a first surface modifying group among the plurality of surface modifying groups is a hydrophobic surface modifying group, and
a second surface modifying group among the plurality of surface modifying groups that is different from the first surface modifying group is a hydrophilic surface modifying group which is shorter than the first surface modifying group,
thereby causing the surface of the porous or particulate material coated over the sensor body to be macroscopically hydrophobic but microscopically hydrophilic.

14. The surface stress sensor according to claim 13, wherein the second surface modifying group is an aminopropyl group, and
the first surface modifying group is an alkyl group which has a longer chain length than the aminopropyl group.

15. The surface stress sensor according to claim 11, wherein a plurality of materials are repeatedly present on the surface of the porous or particulate material and each of the plurality of materials is modified by a surface modifying group of a different type, of the one or the plurality of surface modifying groups.

16. The surface stress sensor according to claim 15, wherein the plurality of materials are at least titania and silica.

17. The surface stress sensor according to claim 11, wherein the porous or particulate material is the porous material, and the porous material has an average pore diameter of 1 mm or less.

18. The surface stress sensor according to claim 17, wherein the average pore diameter of the porous material is 0.1 nm or more and 500 nm or less.

19. A method for producing the surface stress sensor according to claim 11, in which the porous or particulate material is the porous material, and the porous material is synthesized in situ on a surface of the sensor body.

* * * * *